(12) United States Patent
Boutilier et al.

(10) Patent No.: US 7,151,170 B1
(45) Date of Patent: Dec. 19, 2006

(54) USE OF THE BNM3 TRANSCRIPTIONAL ACTIVATOR TO CONTROL PLANT EMBRYOGENESIS AND REGENERATION PROCESSES

(75) Inventors: Kim Boutilier, De Meern (NL); Therese Ouellet, Nepean (CA); Jan Custers, Wageningen (NL); Jiro Hattori, Ottawa (CA); Brian Miki, Ottawa (CA); Michiel Van Lookeren Campagne, Aalter (BE)

(73) Assignees: Plant Research International B.V., Wageningen (NL); Her Majesty the Queen in Right of Canada, as represented by the Minister of Agriculture and Agri-Food Canada, Ontario (CA)

( * ) Notice: Subject to any disclaimer, the term of this patent is extended or adjusted under 35 U.S.C. 154(b) by 375 days.

(21) Appl. No.: 09/980,364

(22) PCT Filed: Jun. 2, 2000

(86) PCT No.: PCT/CA00/00642

§ 371 (c)(1),
(2), (4) Date: Apr. 8, 2002

(87) PCT Pub. No.: WO00/75330

PCT Pub. Date: Dec. 14, 2000

(30) Foreign Application Priority Data

Jun. 2, 1999 (EP) .................................. 99201745

(51) Int. Cl.
*C12N 15/29* (2006.01)
(52) U.S. Cl. ..................................... 536/23.6
(58) Field of Classification Search ............... 536/23.1, 536/23.6; 800/278, 298, 290, 287; 435/468, 435/419, 320.1
See application file for complete search history.

(56) References Cited

FOREIGN PATENT DOCUMENTS

| WO | 97/43427 | 11/1997 |
|---|---|---|
| WO | 98/07842 | 2/1998 |
| WO | 98/37184 | 8/1998 |
| WO | WO 00/70058 | * 11/2000 |

OTHER PUBLICATIONS

Nakamura (Apr. 1999, NCBI Accession No. AB025629).*
Bowie et al, Science 247:1306-1310, 1990.*
McConnell et al, Nature 411 (6838):709-713, 2001.*
Fourgoux-Nicol et al (1999, Plant Molecular Biology 40 :857-872.*
Elliott et al (1996, The Plant Cell 8(2):155-168).*
Nakamura, Y.; "AC AB025629"; Apr. 9, 1999; XP-002120887.
Elliott, R. et al.; "AINTEGUMENTA, an APETALA2-like Gene of Arabidopsis with Pleiotropic Roles in Ovule Development and Floral Organ Growth"; *The Plant Cell*; vol. 8, 1996, pp. 155-168, XP002120889.
Rieger, M. et al.; "AC AL049862"; May 13, 1999, XP-002120888.
Ogas, J. et al.; "Cellular differentiation regulated by gibberellin in the *Arabidopsis thaliana* pickle mutant"; *Science*, vol. 277, Jul. 1997; pp. 91-94; XP-002120890.
Boutilier, K. A. et al.; "Expression of the BnmNAP subfamily of napin genes coincides with the induction of *Brassica* microspore embryogenesis"; *Plant Molecular Biology*; (1994) vol. 26, No. 6, pp. 17111-17723, XP- 002120891.
Custers, Jan B. M. et al.; "Regulation of the inductive phase of microspore embryogenesis in *Brassica napus*"; Acta Hortic (1996), 407 (International Symposium on Brassicas Ninth Crucifer Genetics Workshop, 1994); XP-002120892.
Chaudhury, A. et al.; "Ovule and embryo development, apomixis and fertilization"; *Current Opinion in Plant Biology*, online!, vol. 1, 1998, pp. 26-31; XP-002120893.

* cited by examiner

*Primary Examiner*—Stuart F. Baum
(74) *Attorney, Agent, or Firm*—Merchant & Gould P.C.

(57) ABSTRACT

The present invention provides for a gene obtained during the induction of microspore embryogenisis. The protein encoded by this gene renders plant cells embryongenic, and increases the regenerative capacity of the plant cell. Also disclosed is the regulatory region of this gene and its use for directing the expression of a gene of interest within a suitable host cell.

4 Claims, 11 Drawing Sheets

FIGURE 2

```
BNM3A  GTTCATCTCTCTTCTTTAAGACCAAAACCTTTTTCTCCTCCTCTTCATGCATGAACCCTA   60
BNM3B  ------------------------------------------------------------

BNM3A  ACTAAGTTCTTCTTCTTTTACCTTTTACCAAGAACTCGTTAGATCACTCTCTGAACTCAA  120
BNM3B  --------TTCTTCTTTTACCTTTTACCAAGAACTCGTTAGATCATTTTCTGAACTCGA   51
               ******************************** * ******* *

BNM3A  TGAATAATAACTGGTTAGGCTTTTCTCTCTCTCCTTATGAACAAAATCACCATCGTAAGG  180
BNM3B  TGAATAATAACTGGTTAGGCTTTTCTCTCTCTCCTTATGAACAAAATCACCATCGTAAGG  111
       ************************************************************

BNM3A  ACGTCTACTCTTCCACCACCACAACCGTCGTAGATGTCGCCGGAGAGTACTGTTACGATC  240
BNM3B  ACGTCTGCTCTTCCACCACCACAACCGCCGTAGATGTCGCCGGAGAGTACTGTTACGATC  171
       ****** ******************** ********************************

BNM3A  CGACCGCTGCCTCCGATGAGTCTTCAGCCATCCAAACATCGTTTCCTTCTCCCTTTGGTG  300
BNM3B  CGACCGCTGCCTCCGATGAGTCTTCAGCCATCCAAACATCGTTTCCTTCTCCCTTTGGTG  231
       ************************************************************

BNM3A  TCGTCGTCGATGCTTTCACCAGAGACAACAATAGTCACTCCCGAGATTGGGACATCAATG  360
BNM3B  TCGTCCTCGATGCTTTCACCAGAGACAACAATAGTCACTCCCGAGATTGGGACATCAATG  291
       ***** ******************************************************

BNM3A  GTTGTGCATGCAATAACATCCACAACGATGAGCAAGATGGACCAAAGCTTGAGAATTTCC  420
BNM3B  GTAGTGCATGTAATAACATCCACAATGATGAGCAAGATGGACCAAAACTTGAGAATTTCC  351
       ** ******* ************** ********************  ************

BNM3A  TTGGCCGCACCACCACGATTTACAACACCAACGAAAACGTTGGAGATGGAAGTGGAAGTG  480
BNM3B  TTGGCCGCACCACCACGATTTACAACACCAACGAAAACGTTGGAGATATCGATGGAAGTG  411
       ***********************************************  *******

BNM3A  GCTGTTATGGAGGAGGAGACGGTGGTGGTGGCTCACTAGGACTTTCGATGATAAAGACAT  540
BNM3B  GGTGTTATGGAGGAGGAGACGGTGGTGGTGGCTCACTAGGACTTTCGATGATAAAGACAT  471
       * **********************************************************

BNM3A  GGCTGAGAAATCAACCCGTGGATAATGTTGATAATCAAGAAAATGGCAATGCTGCAAAAG  600
BNM3B  GGCTGAGAAATCAACCCGTGGATAATGTTGATAATCAAGAAAATGGCAATGGTGCAAAAG  531
       *************************************************** *******

BNM3A  GCCTGTCCCTCTCAATGAACTCATCTACTTCTTGTGATAACAACAACGACAGCAATAACA  660
BNM3B  GCCTGTCCCTCTCAATGAACTCATCTACTTCTTGTGATAACAACAACTACAGCAGTAACA  591
       ***********************************************  ******* ****

BNM3A  ACGTTGTTGCCCAAGGGAAGACTATTGATGATAGCGTTGAAGCTACACCGAAGAAAACTA  720
BNM3B  ACCTTGTTGCCCAAGGGAAGACTATTGATGATAGCGTTGAAGCTACACCGAAGAAAACTA  651
       ** *********************************************************

BNM3A  TTGAGAGTTTTGGACAGAGGACGTCTATATACCGCGGTGTTACAAGGCATCGGTGGACAG  780
BNM3B  TTGAGAGTTTTGGACAGAGGACGTCTATATACCGCGGTGTTACAAGGCATCGGTGGACAG  711
       ************************************************************

BNM3A  GAAGATATGAGGCACATTTATGGGATAATAGTTGTAAAAGAGAAGGCCAAACGCGCAAAG  840
BNM3B  GAAGATATGAGGCACATTTATGGGATAATAGTTGTAAACGAGAAGGCCAAACGCGCAAAG  771
       ************************************* *********************

BNM3A  GAAGACAAGTTTATTTGGGAGGTTATGACAAAGAAGAAAAAGCAGCTAGGGCTTATGATT  900
BNM3B  GAAGACAAGTTTATTTGGGAGGTTATGACAAAGAAGAAAAAGCAGCTAGGGCTTATGATT  831
       ************************************************************
```

FIGURE 2(Cont'd)

```
BNM3A    TAGCCGCACTCAAGTATTGGGGAACCACCACTACTACTAACTTCCCCATGAGCGAATATG    960
BNM3B    TAGCCGCACTCAAGTATTGGGGAACCACCACTACTACTAACTTCCCCATGAGCGAATATG    891
         ************************************************************

BNM3A    AAAAAGAGGTAGAAGAGATGAAGCACATGACAAGGCAAGAGTATGTTGCCTCACTGCGCA    1020
BNM3B    AGAAAGAGATAGAAGAGATGAAGCACATGACAAGGCAAGAGTATGTTGCCTCACTTCGCA    951
         *  ***** ***************************************************  ****

BNM3A    GGAAAAGTAGTGGTTTCTCTCGTGGTGCATCGATTTATCGTGGAGTAACAAGACATCACC    1080
BNM3B    GGAAAAGTAGTGGTTTCTCTCGTGGTGCATCGATTTATCGTGGAGTAACAAGACATCACC    1011
         ************************************************************

BNM3A    AACATGGAAGATGGCAAGCTAGGATAGGAAGAGTCGCCGGTAACAAAGACCTCTACTTGG    1140
BNM3B    AACATGGAAGATGGCAAGCTAGGATAGGAAGAGTCGCCGGTAACAAAGACCTCTACTTGG    1071
         ************************************************************

BNM3A    GAACTTTTGGCACACAAGAAGAAGCTGCAGAGGCATACGACATTGCGGCCATCAAATTCA    1200
BNM3B    GAACTTTTGGCACACAAGAAGAAGCTGCAGAGGCATACGACATTGCGGCCATCAAATTCA    1131
         ************************************************************

BNM3A    GAGGATTAACCGCAGTGACTAACTTCGACATGAACAGATACAACGTTAAAGCAATCCTCG    1260
BNM3B    GAGGATTAACCGCAGTGACTAACTTCGACATGAACAGATACAACGTTAAAGCAATCCTCG    1191
         ************************************************************

BNM3A    AAAGCCCTAGTCTTCCTATTGGTAGCGCCGCAAAACGTCTCAAGGAGGCTAACCGTCCGG    1320
BNM3B    AAAGCCCTAGTCTTCCTATTGGTAGCGCCGCAAAACGTCTCAAGGAGGCTAACCGTCCGG    1251
         ************************************************************

BNM3A    TTCCAAGTATGATGATGATCAGTAATAACGTTTCAGAGAGTGAGAATAGTGCTAGCGGTT    1380
BNM3B    TTCCAAGTATGATGATGATCAGTAATAACGTTTCAGAGAGTGAGAATAATGCTAGCGGTT    1311
         *************************************************  *********

BNM3A    GGCAAAACGCTGCGGTTCAGCATCATCAGGGAGTAGATTTGAGCTTATTGCACCAACATC    1440
BNM3B    GGCAAAACGCTGCGGTTCAGCATCATCAGGGAGTAGATTTGAGCTTATTGCAGCAACATC    1371
         ****************************************************  ******

BNM3A    AAGAGAGGTACAATGGTTATTATTACAATGGAGGAAACTTGTCTTCGGAGAGTGCTAGGG    1500
BNM3B    AAGAGAGGTACAATGGTTATTATTACAATGGAGGAAACTTGTCTTCGGAGAGTGCTAGGG    1431
         ************************************************************

BNM3A    CTTGTTTCAAACAAGAGGATGATCAACACCATTTCTTGAGCAACACGCAGAGCCTCATGA    1560
BNM3B    CTTGTTTCAAACAAGAGGATGATCAACACCATTTCTTGAGCAACACGCAGAGCCTCATGA    1491
         ************************************************************

BNM3A    CTAATATCGATCATCAAAGTTCTGTTTCGGATGATTCGGTTACTGTTTGTGGAAATGTTG    1620
BNM3B    CTAATATCGATCATCAAAGTTCTGTTTCGGATGATTCGGTTACTGTTTGTGGAAATGTTG    1551
         ************************************************************

BNM3A    TTGGTTATGGTGGTTATCAAGGATTTGCAGCCCCGGTTAACTGCGATGCCTACGCTGCTA    1680
BNM3B    TTGGTTATGGTGGTTATCAAGGATTTGCAGCCCCGGTTAACTGCGATGCCTACGCTGCTA    1611
         ************************************************************

BNM3A    GTGAGTTTGATTATAACGCAAGAAACCATTATTACTTTGCTCAGCAGCAGCAGACCCAGC    1740
BNM3B    GTGAGTTTGACTATAACGCAAGAAACCATTATTACTTTGCTCAGCAGCAGCAGACCCAGC    1671
         **********  ************************************************

BNM3A    AGTCGCCAGGTGGAGATTTTCCCGCGGCAATGACGAATAATGTTGGCTCTAATATGTATT    1800
BNM3B    ATTCGCCAGGAGGAGATTTTCCCGCGGCAATGACGAATAATGTTGGCTCTAATATGTATT    1731
         *  ********  ************************************************

BNM3A    ACCATGGGGAAGGTGGTGGAGAAGTTGCTCCAACATTTACAGTTTGGAACGACAATTAGA    1860
BNM3B    ACCATGGGGAAGGTGGTGGAGAAGTTGCTCCAACATTTACAGTTTGGAACGACAATTAGA    1791
         ************************************************************
```

FIGURE 2(Cont'd)

```
BNM3A  AAAAATAGTTAAAGATCTTTAGTTATATGCGTTGTTGTGTGCTGGTGAACAGTGTGATAC  1920
BNM3B  AATAATAGTTAAAGATCTTTAGTTATATGCGTTGTTGTGTGGTGTTGAACAGTTTGATAC  1851
       **  ****************************************  ********  ******

BNM3A  TTTGATTATGTTTTTTTCTTTCTCTTTTTCTTTTTCTTGGTTAATTTCTTAAGACTTATT  1980
BNM3B  TTTGATTATGTTTTTT--TTTCTCTTTTTCATTTTGTTGGTTAGTTTCTTAAGACTTATT  1909
       ****************  ************  ****  *******  *************

BNM3A  TTTAGTTTCCATTAGTTGGATAAATTTTCAGACT--------------------------  2014
BNM3B  TTTTGTTTCCATTAGTTGGATAAATTTTCGGACTTAAGGGTCACTTCTGTTCTGACTTCT  1969
       ***  ************************  ****

BNM3A  ----------------------.
BNM3B  GTCTAATACAGAAAAGTTTTCAT                                       1992
```

FIGURE 3

```
BNM3A  MNNNWLGFSLSPYEQNHHRKDVYSSTTTTVVDVAGEYCYDPTAASDESSAIQTSFPSPFG   60
BNM3B  MNNNWLGFSLSPYEQNHHRKDVCSSTTTTAVDVAGEYCYDPTAASDESSAIQTSFPSPFG
       *******************  *****  ********************************

BNM3A  VVVDAFTRDNNSHSRDWDINGCACNNIHNDEQDGPKLENFLGRTTTIYNTNENVGDGSGS  120
BNM3B  VVLDAFTRDNNSHSRDWDINGSACNNIHNDEQDGPKLENFLGRTTTIYNTNENVGDIDGS
       **  *****************  ******************************** ***

BNM3A  GCYGGGDGGGGSLGLSMIKTWLRNQPVDNVDNQENGNAAKGLSLSMNSSTSCDNNNDSNN  180
BNM3B  GCYGGGDGGGGSLGLSMIKTWLRNQPVDNVDNQENGNGAKGLSLSMNSSTSCDNNNYSSN
       ************************************  ****************  * *
                                                         repeat 1
BNM3A  NVVAQGKTIDDSVEATPKKTIESFGQRTSIYRGVTRHRWTGRYEAHLWDNSCKREGQTRK  240
BNM3B  NLVAQGKTIDDSVEATPKKTIESFGQRTSIYRGVTRHRWTGRYEAHLWDNSCKREGQTRK
       * **********************************************************

BNM3A  GRQVYLGGYDKEEKAARAYDLAALKYWGTTTTTNFPMSEYEKEVEEMKHMTRQEYVASLR  300
BNM3B  GRQVYLGGYDKEEKAARAYDLAALKYWGTTTTTNFPMSEYEKEIEEMKHMTRQEYVASLR
       ******************************************  ***************
           repeat 2
BNM3A  RKSSGFSRGASIYRGVTRHHQEGRWQARIGRVAGNKDLYLGTFGTQEEAAEAYDIAAIKF  360
BNM3B  RKSSGFSRGASIYRGVTRHHQEGRWQARIGRVAGNKDLYLGTFGTQEEAAEAYDIAAIKF
       ************************************************************

BNM3A  RGLTAVTNFDMNRYNVKAILESPSLPIGSAAKRLKEANRPVPSMMMISNNVSESENSASG  420
BNM3B  RGLTAVTNFDMNRYNVKAILESPSLPIGSAAKRLKEANRPVPSMMMISNNVSESENNASG
       ******************************************************* ***

BNM3A  WQNAAVQHHQGVDLSLLHQHQERYNGYYYNGGNLSSESARACFKQEDDQHHFLSNTQSLM  480
BNM3B  WQNAAVQHHQGVDLSLLQQHQERYNGYYYNGGNLSSESARACFKQEDDQHHFLSNTQSLM
       *****************  *****************************************

BNM3A  TNIDHQSSVSDDSVTVCGNVVGYGGYQGFAAPVNCDAYAASEFDYNARNHYYFAQQQQTQ  540
BNM3B  TNIDHQSSVSDDSVTVCGNVVGYGGYQGFAAPVNCDAYAASEFDYNARNHYYFAQQQQTQ
       ************************************************************

BNM3A  QSPGGDFPAAMTNNVGSNMYYHGEGGGEVAPTFTVWNDN  579
BNM3B  HSPGGDFPAAMTNNVGSNMYYHGEGGGEVAPTFTVWNDN
        **************************************
```

FIGURE 5

AP2 DOMAIN REPEAT 1

```
BNM3  TSIYRGVTRHRWTGRYEAHLWDNSCKREGQTRKGRQVYLGGYDKEEKAARAYDLAALKYWGTTTTNFPMSEYEKEV
ANT   T*Q***************************F*KHS*********M********PS*H***SAEN*Q**I
ZM    T***************************ER**S*********************F*P****QV*N****L
GL15  S*Q******FY*R****W*S*I**--C-------*K********F*TAQA*******Q**I*FR*LNADI**TLDD*KD*M
AP2   S*Q******FY*R****W*S*I**--C-------*K********F*TAHA*******R**I*FR*VEADI**NIDD*DDDL
```

LINKER

```
BNM3  EEMKHMTRQEYVASLRRKSSGFSRG
ANT   *DN****H*********
ZM    ****S******FI************
GL15  KK**DLSKE*F*LV**QGAV**
AP2   KQ*TNL*KE*F*HV***Q*TP
```

AP2 DOMAIN REPEAT 2

```
BNM3  ASIYRGVTRHHQHGRWQARIGRVAGNKDLYLGTFGTQEEAAEAYDIAAIKFRGLTAVTNFDMNRYNVKA
ANT   ***********************************************V*******TN****IT**D*DR
ZM    ****************************************S*******N****L*S**D*ES
GL15  S*RF*****-Q*KC*K*E****QLM*K*YV***LYD*ET***Q***K****CY*KE******AQS*DKEL
AP2   S*K******-L*KCE*M*QFL*K*YV***L*D*EV*RKD**CN*KD*****PSI*DEEL
```

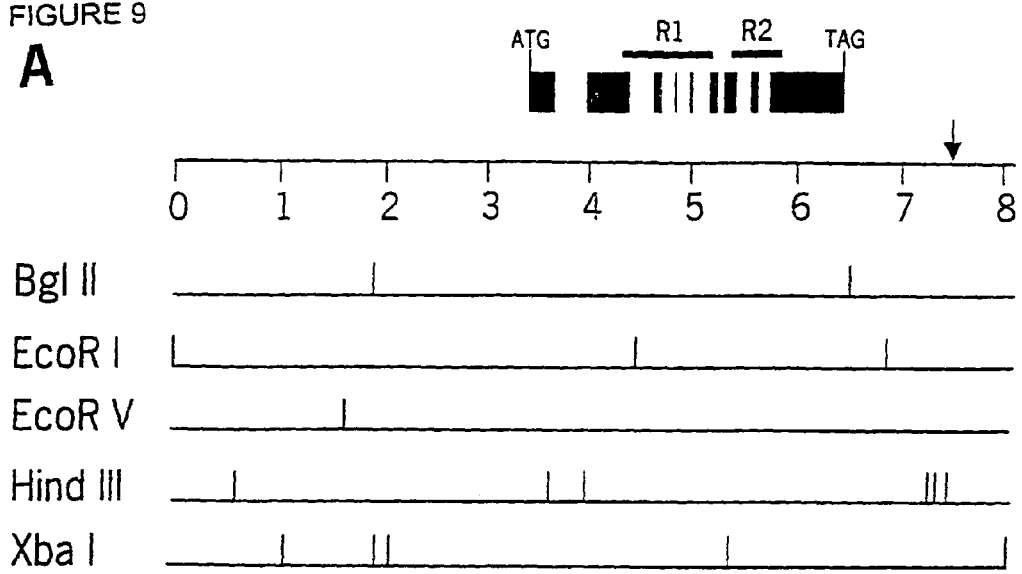
FIGURE 9
A
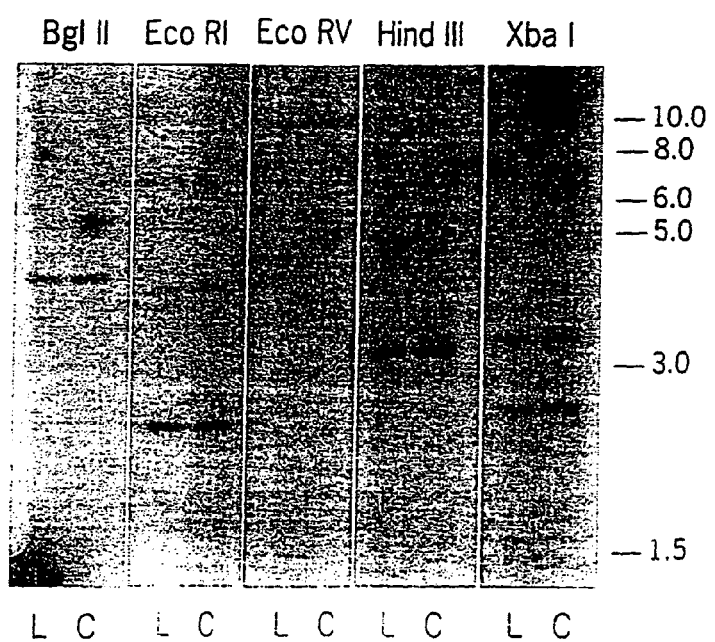

USE OF THE BNM3 TRANSCRIPTIONAL ACTIVATOR TO CONTROL PLANT EMBRYOGENESIS AND REGENERATION PROCESSES

BACKGROUND OF THE INVENTION

A typical angiosperm seed consists of three major components, the embryo, the endosperm and the maternal seed coat. Seed development begins with a double fertilization event, in which one sperm cell nucleus fuses with the egg cell nucleus to form the embryo, and a second sperm cell nucleus fuses with two central cell nuclei to form the endosperm. Embryo development itself can be separated into three developmental phases. The first phase of embryo development is one of cell division and morphogenesis, which serves to establish the major tissue types and organ systems of the mature plant. The second phase encompasses a period of rapid cell expansion and is characterized by the synthesis of storage reserves that sustain the embryo during germination and early seedling development. In the final phase of embryo development, the embryo becomes desiccated and enters into a period of developmental arrest or dormancy. All of the above events normally take place while the seed remains attached to the maternal plant.

Many plant species are capable of producing embryos in the absence of fertilization. This process of asexual embryo development may occur naturally, for example on the leaf margins of *Bryophyllum* (Yarborough, 1923) and *Malaxis* (Taylor, 1967), or within the ovule of apomictic plants (Koltunow, 1995). Apomixis refers to the production of a seed from the maternal ovule tissues in the absence of egg cell fertilization. Asexual embryo development may also be induced in vitro from gametophytic or somatic tissue (Mordhorst et al., 1997) or, as shown recently, may be induced by genetic modification of gene expression (Ogas et al., 1997; Lotan et al., 1998).

Three major mechanisms of apomixis, diplospory, apospory and adventitious embryony, have been observed. Each mechanism differs with respect to the source of the cell that gives rise to the embryo and with respect to the time during ovule development at which the apomictic process is initiated. Diplospory and apospory are considered gametophytic forms of apomixis as they involve the formation of diploid embryo sacs. Adventitious embryony does not involve the production of a mitotically-derived embryo sac.

In diplospory, the megaspore mother cell does not undergo normal meiosis, but rather divides mitotically to produce a diploid embryo sac instead of the normal haploid embryo sac. One of the cells of the embryo sac functions as the egg cell and divides parthenogenetically (without fertilization) to form an embryo. In some species the unreduced polar nuclei of the embryo sac may fuse to form the endosperm (autonomous endosperm production), the nutritive tissue of the seed, while in other species pollination is necessary for endosperm production (pseudogamy).

In aposporous apomicts, parthenogenic embryos are produced from additional cells, the aposporous initials, that differentiate from the nucellus. As with the megagametophyte of diplosporous species, the aposporous initial undergoes mitotic divisions to produce a diploid embryo sac. Aposporous embryos are not derived from the megagametophyte and can therefore co-exist within a single ovule with sexually-derived embryos. Autonomous production of endosperm is rare in aposporous species. Aposporous apomicts therefore depend on fertilization of the polar nuclei of a meiotically-derived embryo sac for the production of endosperm.

With adventitious embryony, embryos are formed directly from sporophytic ovule tissue, such as the integuments or nucellus, via parthenogenesis. Seeds derived from species exhibiting adventitious embryony generally contain multiple asexually-derived embryos and may also contain a single sexually-derived embryo. Plants exhibiting adventitious embryo also rely on the presence of a meiotically-derived embryo sac within the same ovule for endosperm formation.

In most plant species, the apomictic trait appears to be under the control of a single dominant locus. This locus may encode one or more developmental regulators, such as transcription factors, that in sexually reproducing plants function to initiate gene expression cascades leading to embryo sac and/or embryogenesis, but which are heterochronically or ectopically expressed in apomictic plants (Peacock, 1995; Koltunow, 1993; Koltunow et al, 1995).

Apomixis is a valuable trait for crop improvement since apomictic seeds give rise to clonal offspring and can therefore be used to genetically fix hybrid lines. The production of hybrid seed is a labour intensive and costly procedure as it involves maintaining populations of genetically pure parental lines, the use of separate pollen donor and male-sterile lines, and line isolation. Production of seed through apomixis avoids these problems in that once a hybrid has been produced, it can be maintained clonally, thereby eliminating the need to maintain and cross separate parental lines. The use of apomictic seed also provides a more cost effective method of multiplying vegetatively-propagated crops, as it eliminates the use of cuttings or tissue culture techniques to propagate lines, reduces the spread of diseases which are easily transmitted through vegetatively-propagated tissues, and in many species reduces the size of the propagule leading to lower shipping and planting costs.

Although apomixis occurs in a wide range of plant species, few crop species are apomictic. Attempts to introduce apomictic traits into crop species by introgression from wild relatives (Ozias-Akins, et al., 1993; WO 97/10704; WO 97/11167) or through crosses between related, but developmentally divergent sexual species (WO 98/33374), have not yielded marketable products. Other approaches have focused on the identification of gene sequences that may be used to identify or manipulate apomictic processes (WO 97/43427; WO 98/36090), however these approaches have not led to methods for the routine production of apomictic plants.

Mutagenesis approaches have also been attempted to convert sexually reproducing plants such as *Arabidopsis thaliana* (*arabidopsis*) into apomictic plants (Peacock et al., 1995). For example, a number of recessive "fertilization-independent seed" (fis) mutants have been identified that initiate partial embryo and/or endosperm at a low frequency in the absence of fertilization (Chaudhury et al., 1997). However, a number of additional parameters need to be modified in order to obtain true diploid apomictic seed using fis mutants.

Asexually-derived embryos can be induced to form in culture from many gametophytic and somatic plant tissues (Yeung, 1995). Somatic embryos can be obtained from culture of somatic tissues by treating them with plant growth regulators, such as auxins, or auxins in combination with cytokinins. Embryos can also be induced to form in culture from the gametophytic tissues of the ovule (gynogenesis) and the anther (androgenesis, pollen or microspore embryogenesis), either by the addition of plant growth regulators or by a simple stress treatment.

Several mutants have been identified that may be used to induce efficient production of embryos in vitro. These include recessive *arabidopsis* mutants with altered shoot meristems, for example primordia timing (pt), clavata (clv)1 and clv3, which were shown to enhance embryogenic callus formation when seedlings were germinated in the presence of auxin (Mordhorst et al., 1998). The altered expression of two *arabidopsis* genes, LEAFY COTYLEDON (LEC1; WO 98/37184, Lotan et al., 1998) and pickle, have been shown to promote the production of somatic embryos in the absence of added growth regulators. The LEC1 gene encodes a homologue of the HAP3 subunit of a CCAAT box-binding transcription factor (CBF). The LEC1 gene controls many aspects of zygotic embryo development including desiccation tolerance and cotyledon identity. Ectopic over-expression of the LEC1 gene in a led mutant background results in the production of 2 transgenic lines that occasionally form embryo-like structures on leaves. These embryo-like structures express genes, such as those encoding seed storage proteins and oil body proteins, which are normally preferentially expressed in developing embryos. Plants containing a recessive mutant PICKLE gene produce a thickened, primary root meristem. Mutant pickle roots produce embryo-forming callus when the root tissue is separated from the rest of the plant and placed on minimal medium without growth regulators (Ogas et al., 1997). Mutant pickle roots show morphological characteristics of developing seeds, such as oil bodies and, as with LEC1 over-expressers, accumulate genes preferentially expressed in developing seeds.

Efficient production of apomictic seed is only likely to be realised through the identification and subsequent modification of developmental regulators, such as transcription factors, that are known to activate gene expression cascades leading to embryogenesis in both sexually-reproducing and apomictic plants. The present invention addresses this need by providing methods for the production of apomictic seeds comprising ectopic over-expression of an embryo-expressed AP2 domain containing transcription factor, BNM3 or its homologs.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to asexual embryo formation and regeneration in plants. More specifically, it relates to processes for producing asexually-derived embryos, and for enhancing regeneration capacity in plants.

According to the present invention there is provided an isolated DNA molecule comprising a nucleotide sequence that:

hybridizes to SEQ ID NO:5 or 6, not including the AP2 repeat1-linker-AP2 repeat2 region, under moderate or stringent conditions;

hybridizes to SEQ ID NO:1 or 3, not including the AP2 repeat 1-linker-AP2 repeat2 region, under stringent conditions;

comprises at least 27 contiguous nucleotides of SEQ ID NO's:1, 3, 5 or 6; or that exhibits at least 70% similarity with the nucleotide sequence defined by SEQ ID NO's:1, 3, 5 or 6.

This invention further relates to an isolated DNA molecule that hybridizes to SEQ ID NO's: 1, 3, 5 or 6, not including the AP2 repeat1-linker-AP2 repeat2 region, under moderate or stringent conditions, and comprises a nucleic acid sequence encoding a protein, wherein the protein when present at a sufficient level within a plant cell renders the cell embryogenic, increases the regenerative capacity of the plant cell, or both renders the cell embryogenic and increases the regenerative capacity of the plant cell. Included within the present invention is the isolated DNA molecule as just defined comprising a nucleotide sequence that hybridizes to nucleotides 1–2014 of SEQ ID NO:1, 1–2011 of SEQ ID NO:3, 1620–4873 of SEQ ID NO:5, or nucleotides 2026–5035 of SEQ ID NO:6, not including the AP2 repeat1-linker-AP2 repeat2 region, under moderate or stringent conditions. Also included within the present invention is a vector comprising the isolated DNA molecule as defined above, wherein the isolated DNA molecule is under control of a regulatory element that directs expression of said DNA in a plant cell. The regulatory element may be a constitutive, inducible, tissue specific or a developmental active, regulatory element.

This invention also embraces a transformed plant cell, a transformed plant, or seed obtained from a transformed plant, each comprising the vector as defined above This invention relates to an isolated protein encoded by an isolated DNA molecule that hybridizes to the nucleotide sequence defined by SEQ ID NO:1, 3, 5 or 6, not including the AP2 repeat1-linker-AP2 repeat2 region, under moderate or stringent conditions, wherein the protein, when present at a sufficient level within a plant cell renders the cell embryogenic, or increases the regenerative capacity of the plant cell. Also included is a protein encoded by an isolated DNA molecule that hybridizes to nucleotides 1620–4873 of SEQ ID NO:5, or nucleotides 2026–5035 of SEQ ID NO:6, not including the AP2 repeat1-linker-AP2 repeat2 region, under moderate or stringent conditions, or to the nucleotide sequence as defined within SEQ ID NO:1 or 3 under moderate or stringent conditions. This invention also embraces an isolated DNA molecule that encodes a protein as defined by SEQ ID NO:2, SEQ ID NO:4 or SEQ ID NO:7. The invention also pertains to a protein comprising at least 70% homology with the amino acid sequence of SEQ ID NO:2, SEQ ID NO:4 or SEQ ID NO:7, or comprises from about 30 to about 541 amino acids of the sequence disclosed in SEQ ID NO:2, or comprises from about 30 to about 561 amino acids of the sequence disclosed in SEQ ID NO:4.

The present invention is also directed to a method of producing asexually derived embryos comprising:

i) transforming a plant cell with a vector comprising an isolated DNA molecule that hybridizes to SEQ ID NO's: 1, 3, 5, or 6, not including the AP2 repeat1-linker-AP2 repeat2 region, under moderate or stringent conditions and which encodes a protein that when present at a sufficient level within the plant cell renders the plant cell embryogenic, or increases the regenerative capacity of the plant cell, or that comprises a nucleotide sequence that hybridizes to nucleotides 1620–4873 of SEQ ID NO:5, or nucleotides 2026–5035 of SEQ ID NO:6, not including the AP2 repeat1-linker-AP2 repeat2 region, under moderate or stringent conditions, or to the nucleotide sequence as defined within SEQ ID NO:1 or 3 under moderate or stringent conditions;
ii) growing the plant cell to produce transformed tissue;
iii) selecting the transformed tissue for occurrence of the isolated DNA molecule; and
iv) assaying the transformed tissue for asexual embryo formation.

This invention also relates to the above method where the step of assaying (step iv)) involves assaying for somatic embryos, gametophytically-derived embryos, adventitious embryony, diplospory, or for haploid parthenogenesis of the embryo sac.

The present invention also embraces a method of producing an apomictic plant comprising:
i) transforming a plant cell with a vector comprising an isolated DNA molecule that hybridizes to nucleotides 1–2014 of SEQ ID NO:1, nucleotides 1–2011 of SEQ ID NO:3, nucleotides 1620–4873 of SEQ ID NO:5, or nucleotides 2026–5035 of SEQ ID NO:6, not including the AP2 repeat1-linker-AP2 repeat2 region, under moderate or stringent conditions and which encodes a protein that when present at a sufficient level within said plant cell renders the plant cell embryogenic, or increases the regenerative capacity of the plant cell;
ii) selecting the transformed plant for occurrence of the isolated DNA molecule; and
iii) assaying the transformed plant for asexual embryo formation.

This invention also relates to the above method where the step of assaying (step iii)) involves assaying for asexually-derived embryos, somatic embryos, gametophytically-derived embryos, adventitious embryony, diplospory, or for haploid parthenogenesis of the embryo sac.

The present invention is also directed to a method of producing asexually derived embryos comprising:
i) transiently transforming a plant cell with a vector comprising an isolated DNA molecule that hybridizes to nucleotides 1–2014 of SEQ ID NO:1, nucleotides 1–2011 of SEQ ID NO:3, nucleotides 1620–4873 of SEQ ID NO:5, or nucleotides 2026–5035 of SEQ ID NO:6, not including the AP2 repeat1-linker-AP2 repeat2 region, under moderate or under stringent conditions and which encodes a protein that when present at a sufficient level within the plant cell renders the plant cell embryogenic, or increases the regenerative capacity of the plant cell;
ii) growing the transiently transformed plant cell to produce transiently transformed tissue;
iii) assaying the transiently transformed tissue for asexual embryo formation.

This invention is directed to the above method where the step of assaying (step iii)) involves assaying for asexually-derived embryos, somatic embryos, gametophytically-derived embryos, adventitius embryony, diplospory, or for haploid parthenogenesis of the embryo sac.

The present invention also presents a method of modifying the regenerative capacity of a plant comprising
i) transforming a plant cell with a vector comprising an isolated DNA molecule that hybridizes to SEQ ID NO:5 or SEQ ID NO:6 under moderate or stringent conditions and which encodes a protein that when present at a sufficient level within the plant cell renders the plant cell embryogenic, or increases the regenerative capacity of said plant cell, or that comprises a nucleotide sequence that hybridizes to nucleotides 1620–4873 of SEQ ID NO:5, or nucleotides 2026–5035 of SEQ ID NO:6, not including the AP2 repeat1-linker-AP2 repeat2 region, under moderate or under stringent conditions, or to the nucleotide sequence as defined within nucleotides 1–2014 of SEQ ID NO:1, or nucleotides 1–2011 of SEQ ID NO:3 under stringent conditions;
ii) growing the transformed plant cell to produce transformed tissue; and
iii) assaying the transformed tissue for enhanced regeneration as compared to wild type tissue.

This invention also embraces the above method wherein step iii) includes assaying in the absence of a growth regulator.

The present invention also relates to a method of modifying the regenerative capacity of a plant comprising;
i) transiently transforming a plant cell with a vector comprising an isolated DNA molecule that hybridizes to SEQ ID NO:5 or SEQ ID NO:6 under moderate or stringent conditions and which encodes a protein that when present at a sufficient level within the plant cell renders the plant cell embryogenic, or increases the regenerative capacity of the plant cell, or that comprises a nucleotide sequence that hybridizes to nucleotides 1620–4873 of SEQ ID NO:5, or nucleotides 2026–5035 of SEQ ID NO:6, not including the AP2 repeat1-linker-AP2 repeat2 region, under moderate or under stringent conditions, or to the nucleotide sequence as defined within SEQ ID NO:1 or 3 under stringent conditions;
ii) growing the transiently transformed plant cell to produce transiently transformed tissue;
iii) assaying the transformed tissue for enhanced regeneration as compared to wild type tissue.

This invention also embraces the above method wherein step iii) includes assaying in the absence of a growth regulator.

The present invention also relates to a method of selecting a transformed plant comprising;
i) transforming a normally non-regenerative plant with a vector comprising an isolated DNA molecule that hybridizes to SEQ ID NO:5 or SEQ ID NO:6 under moderate stringent conditions and which encodes a protein that when present at a sufficient level within the plant cell renders the plant cell embryogenic, or increases the regenerative capacity of said plant cell, or that comprises a nucleotide sequence that hybridizes to nucleotides 1620–4873 of SEQ ID NO:5, or nucleotides 2026–5035 of SEQ ID NO:6, not including the AP2 repeat1-linker-AP2 repeat2 region, under moderate or under stringent conditions, or to the nucleotide sequence as defined within SEQ ID NO:1 or 3 under stringent conditions; and
ii) determining whether the transformed plant is able to regenerate under conditions in which the normally non-regenerative plant does not regenerate.

The present invention is also directed to an isolated DNA molecule comprising a DNA sequence that exhibits at least about 70% similarity with nucleotides 1–1619 of SEQ ID NO:5, or nucleotides 1–2025 of SEQ ID NO:6, or that comprises at least 22 contiguous nucleotides within nucleotides 1–1619 of SEQ ID NO:5 or 1–2025 of SEQ ID NO:6. Also included within the scope of the present invention is a vector comprising the isolated DNA molecule as just defined, operably associated with a gene of interest, wherein the isolated DNA molecule directs the expression of the gene of interest within a plant cell. The gene of interest may be heterologous with respect to the isolated DNA molecule. The gene of interest may be selected from the group consisting of a pharmaceutically active protein, antibody, industrial enzyme, protein supplement, nutraceutical, storage protein, animal feed and animal feed supplement. This invention also includes a transformed plant cell, a transformed plant, or seed obtained from the transformed plant, comprising the vector as just defined.

Furthermore, the present invention includes a method for directing the expression of a gene of interest within a developing embryo of a plant comprising transforming said plant with a vector containing an isolated DNA molecule that exhibits at least about 70% similarity with nucleotides 1–1619 of SEQ ID NO:5, or nucleotides 1–2025 of SEQ ID NO:6, or that comprises at least 22 contiguous nucleotides within nucleotides 1–1619 of SEQ ID NO:5 or nucleotides 1–2025 of SEQ ID NO:6.

This invention also pertains to a method of producing a protein of interest comprising
  i) transforming a plant with at least one vector, comprising an isolated DNA molecule that hybridizes to SEQ ID NO:5 or SEQ ID NO:6 under moderate or stringent conditions and which encodes a protein that when present at a sufficient level within the plant cell renders the plant cell embryogenic, or increases the regenerative capacity of said plant cell, or that comprises a nucleotide sequence that hybridizes to nucleotides 1620–4873 of SEQ ID NO:5, or nucleotides 2026–5035 of SEQ ID NO:6, not including the AP2 repeat1-linker-AP2 repeat2 region, under moderate or under stringent conditions, or to the nucleotide sequence as defined within SEQ ID NO:1 or 3 under stringent conditions to produce a transformed plant;
  ii) selecting the transformed plant for occurrence of the isolated DNA molecule; and
  iv) growing the transformed plant in order to produce the protein of interest, wherein expression of the protein of interest is induced by the expression product of said isolated DNA.

This method may also comprise transforming the plant with a second vector comprising a nucleotide sequence encoding the protein of interest under the control of a regulatory element, wherein the regulatory element induced by the expression product of the isolated DNA. Furthermore, this method may also be used to produce a protein of interest wherein the protein of interest is a native protein.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 2 shows the alignment of the DNA sequences depicted in SEQ ID NO:1 (BNM3A) and SEQ ID NO:3 (BNM3B). The ATG and TAG translation initiation and translation termination codons are shown in bold. Identical nucleotides are indicated by (*) and gaps are indicated by (–).

FIG. 3 shows the alignment of the predicted protein sequences (SEQ ID NO:2 (BNM3A); SEQ ID NO:4 (BNM3B)) encoded by the DNA of SEQ ID NO:1 (BNM3A) and SEQ ID NO:3 (BNM3B). The amino acid sequence of the first AP2 domain repeat (repeat 1) and the second AP2 domain repeat (repeat 2), are shown in bold. Identical amino acids are indicated by an asterisk (*) and mismatches by a dot (.) below the sequence alignment.

FIG. 5 shows the alignment of the predicted protein sequence encoded by the DNA of SEQ ID NO:1 (BNM3A) with the predicted protein sequences of other AP2 domain proteins. The amino acid sequence of BNM3A, beginning at position 208, and spanning the first AP2 domain repeat (AP2 domain repeat 1; amino acids 208–284 of SEQ ID NO:2), the second AP2 domain repeat (AP2 domain repeat 2; amino acids 310–378 of SEQ ID NO:2), and the linker region lying between the two repeats (linker; amino acids 285–309 of SEQ ID NO:2), was aligned with the amino acid sequence of other proteins containing two AP2 domains: ANT (AP2 domain repeat 1 (amino acids 281–357 of SEQ ID NO:15); linker (amino acids 358–382 of SEQ ID NO:15); AP2 domain repeat 2 (amino acids 383–451 of SEQ ID NO:15)); ZM (AP2 domain repeat 1 (amino acids 138–214 of SEQ ID NO:16); linker (amino acids 215–239 of SEQ ID NO:16); AP2 domain repeat 2 (amino acids 240–308 of SEQ ID NO:16)); GL15 (AP2 domain repeat 1 (amino acids 111–177 of SEQ ID NO:17); linker (amino acids 178–202 of SEQ ID NO:17); AP2 domain repeat 2 (amino acids 203–270 of SEQ ID NO:17)); AP2 (AP2 domain repeat 1 (amino acids 129–195 of SEQ ID NO:18); linker (amino acids 196–220 of SEQ ID NO:18); AP2 domain repeat 2 (amino acids 221–288 of SEQ ID NO:18). The amino acid similarity in this region ranges from 53% for APETALA2 to 80% for ZMMHCF1. Identical amino acids are indicated by (*) and gaps are indicated by (–). Protein names are indicated on the left and are abbreviated as follows: ANT, AINTEGUMENTA (accession number U41339); ZM, ZMMHCF1 (accession number Z47554); GL15, GLOSSY15 (accession number U41466); AP2, APETALA2 (accession number U12546).

FIG. 6A shows the pattern of BNM3 expression in microspore embryo cultures. RNA was isolated from late uninucleate microspores and early binucleate pollen at the time of collection (pollen 0 d), after four days in culture at 32° C. (+embryo), after four days in culture at 25° C. (pollen 4 d), after one day of culture at 25° C., followed by three days of culture at 32° C. (−embryo) and microspore-derived embryos at the globular, heart, torpedo, 21 day old cotyledon (21 d cot), 28 day old cotyledon (28 d cot) and 42 day old cotyledon (42 d cot) stage of development. BNM3 expression is detected in embryogenic microspores and developing microspore-derived embryos, but is absent from developing microspores and pollen collected prior to tissue culture and in non-embryogenic samples. The exposure time was seven days. FIG. 6B shows that BNM3 gene expression is detected in developing seeds. Seeds were collected at various days after pollination (DAP). These points in development correspond approximately to the globular (7 d), heart (14 d), torpedo (18 d), early cotyledon (21 d), mid cotyledon (28 d, 35 d) and late cotyledon (42 d) stages of development. The exposure time was 14 days. FIG. 6C shows that BNM3 gene expression is not detected in non-seed tissues. Roots and leaves were collected from 14 day old greenhouse grown plants. Entire flowers as well as excised anthers and pistils were collected from opened flower buds just prior to anthesis. Small and large buds refer to closed flower buds of less than 5 mm or greater than 5 mm in length, respectively. Siliques were collected 16 days after pollination. The exposure time was 14 days.

FIG. 7A shows embryo structures on the leaf margin of a *Brassica* T1 seedling. FIG. 7B shows embryo structures on the petiole of an *arabidopsis* T2 seedling. FIG. 7C shows embryo structures on the cotyledon of an *arabidopsis* T1 seedling. FIG. 7D shows a scanning electron micrograph of the abaxial side of an *arabidopsis* T1 cotyledon. Note the bipolar nature of the embryos, as well as the emergence of a secondary embryo from the surface of a primary embryo (asterisk). FIG. 7E shows a semi-thin section through one of the cotyledons of the T1 seedling shown in (FIG. 7C). Note the presence of all the major organs and tissue elements of embryo, as well as the development of new embryos on the flanks of the shoot apical meristems and the cotyledons.

FIG. 8A shows wild-type and transgenic leaf and hypocotyl explants on medium containing growth regulators. FIG. 8B shows wild-type and transgenic roots on medium containing growth regulators. FIG. 8C shows wild-type and transgenic leaf and hypocotyl explants on medium without growth regulators. FIG. 8D shows wild-type and transgenic root explants on medium without growth regulators FIG. 9 shows characterization of the AtBBM gene; the *arabidopsis* orthologue of BNM3. FIG. 9A shows the position of the AtBBM sequence and selected restriction endonuclease sites on approximately 8 kb of overlapping *Arabidopsis thaliana* ecotype C24 genomic DNA. The predicted protein coding region of the single *arabidopsis* BNM3 homologue spans positions 3426 to 6435 of the genomic sequence. The exons of the predicted coding region are shown as black boxes above the restriction map. A vertical arrow at position 7479 indicates the start of the IXR3 (Irregular xylem3) sequence. The horizontal scale bar is in kilobases. FIG. 9 B shows that the *arabidopsis* AtBBM genomic clones and the *arabidopsis* homologue identified through DNA gel blot analysis using a *Brassica napus* BNM3 cDNA probe are the same. Genomic DNA from *arabidopsis* ecotypes Landsberg erecta (L) and Columbia (C) was digested with the restricted enzymes shown in (A) and hybridised to a full-length BNM3A cDNA probe (SEQ ID NO1). Comparison of the restriction map shown in (A) with the pattern of hybridising restriction fragments indicates that the fill-length *Brassica* cDNA probe detects a single *Arabidopsis* homologue under moderate stringency wash conditions (0.2×SSC, 0.1% SDS at 25° C.). The molecular size marker (in kilobases) is indicated to the right of the blot.

DESCRIPTION OF PREFERRED EMBODIMENT

Figure 1:
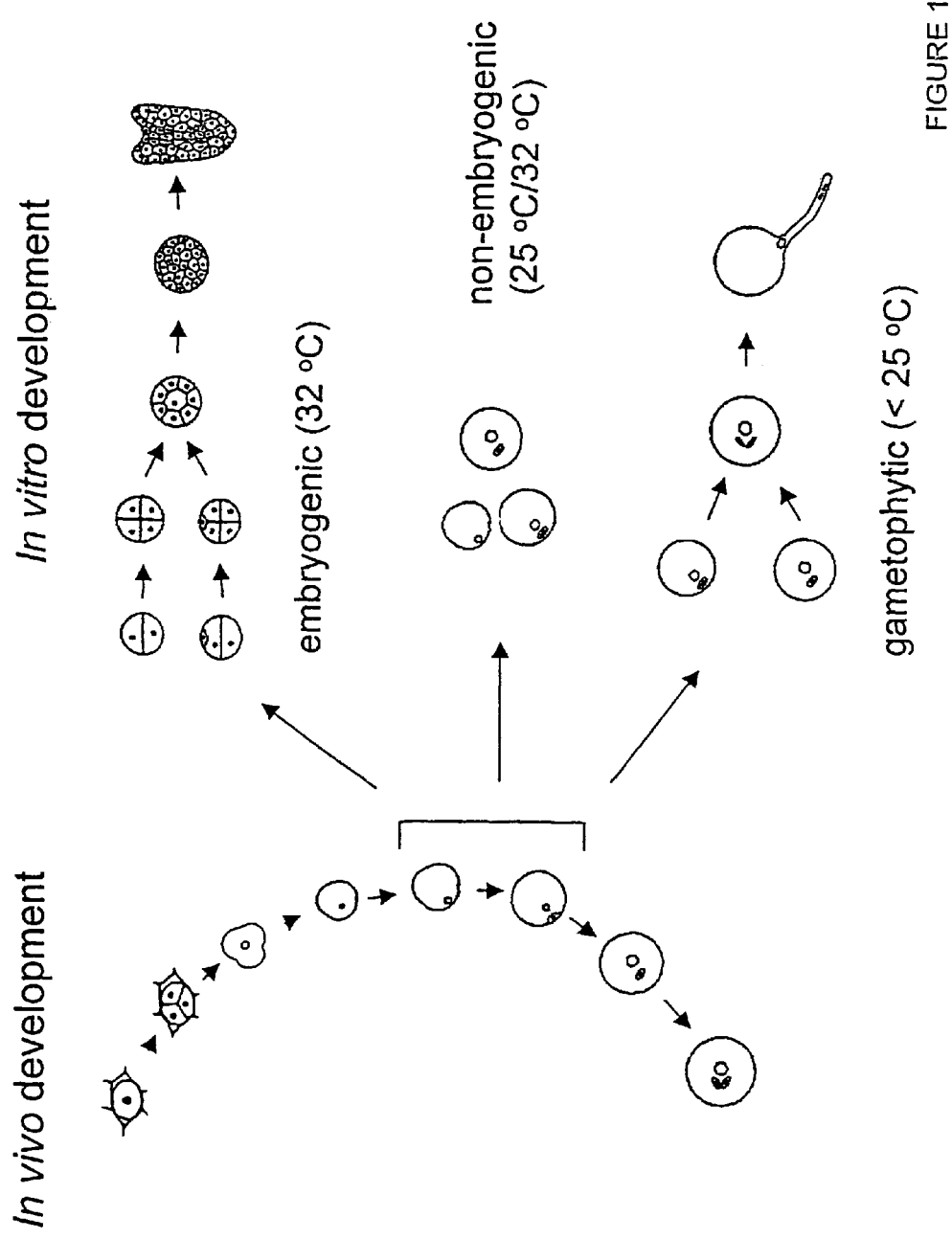
FIG. 1 shows a schematic representation of the effect of culture temperature on the developmental fate of isolated microspores and pollen of Brassica napus. Late uninucleate microspores and early binucleate pollen cultured at 25° C. or lower continue to divide and form functional pollen grains (gametophytic), while the same microspores and pollen cultured at 32° C. undergo numerous sporophytic divisions, leading to the formation of haploid embryos (embryogenic). Late uninucleate microspores and early binucleate pollen cultured for one day at 25° C., followed by culture at 32° C. may undergo gametophytic divisions, but form neither embryos nor mature pollen grains (non-embryogenic).

The present invention relates to asexual embryo formation and regeneration in plants. More specifically, it relates to processes for producing asexually-derived embryos, and for enhancing regeneration capacity in plants. The present invention also relates to heterologous protein production systems in plants, and the uses thereof.

The following description is of a preferred embodiment by way of example only and without limitation to the combination of features necessary for carrying the invention into effect.

Genes preferentially expressed during the induction of *Brassica napus* c.v. Topas microspore embryogenesis were isolated via subtractive screening. Seven independent cDNA clones, comprising six unique DNA sequences were found to be differentially expressed between cDNA libraries prepared from embryogenic and non-embryogenic microspore cultures. Several of these BNM (for *Brassica napus* microspore embryo) clones, BNM3A (SEQ ID NO:1) and BNM3B (SEQ ID NO:3), were characterized as described herein. BNM3A and BNM3B encode the amino acid sequences disclosed in SEQ ID NO:2, and SEQ ID NO:4, respectively. The genomic sequence of BNM3A (SEQ ID NO:5), including the regulatory region (nucleotides 1–1619 of SEQ ID NO:5), was also obtained. The *arabidopsis* orthologue of the BNM3 gene, called AtBBM, was also identified. The genomic sequence of AtBBM is depicted in SEQ ID NO:6 while the predicted amino acid sequence is shown in SEQ ID NO:7.

"Regeneration", as used herein, refers to a morphogenetic response that results in the production of new tissues, organs, embryos, whole plants or fragments of whole plants that are derived from a single cell, or a group of cells. Regeneration may proceed indirectly via a callus phase or directly, without an intervening callus phase. "Regenerative capacity" refers to the ability of a plant cell to undergo regeneration.

By "embryogenic cell", it is meant a cell that has completed the transition from either a somatic or a gametophytic cell to a state where no further applied stimuli are necessary to produce an embryo.

By "regulatory element" it is meant those that include developmentally regulated, tissue specific, inducible and constitutive regulatory elements. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well, such regulatory elements are considered "tissue specific". Regulatory elements may be found either upstream, within, downstream, or a combination thereof, of the coding region of a gene.

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

A constitutive regulatory element directs the expression of a gene throughout the various parts of a plant and continuously throughout plant development. Examples of known constitutive regulatory elements include promoters associated with the CaMV 35S transcript. (Odell et al., 1985, *Nature*, 313: 810–812), the rice actin 1 (Zhang et al, 1991, *Plant Cell*, 3: 1155–1165) and triosephosphate isomerase 1 (Xu et al, 1994, *Plant Physiol.* 106: 459–467) genes, the maize ubiquitin 1 gene (Cornejo et al, 1993, *Plant Mol. Biol.* 29: 637–646), the *Arabidopsis* ubiquitin 1 and 6 genes (Holtorf et al, 1995, *Plant Mol. Biol.* 29: 637–646), and the tobacco translational initiation factor 4A gene (Mandel et al, 1995 *Plant Mol. Biol.* 29: 995–1004).

By "gene of interest" it is meant any gene that is to be expressed in a transformed plant. Such a gene of interest may include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases chitinases, invertases, lipases, cellulases, xylanases, enzymes involved in oil biosynthesis etc. Other protein supplements, nutraceuticals, or a value-added products include native or modified seed storage proteins and the like.

The present invention is further directed to a chimeric gene construct containing a DNA of interest operatively linked to a regulatory element of the present invention. Any exogenous gene, or gene of interest, can be used and manipulated according to the present invention to result in the expression of the exogenous gene.

The activation of the expression of a gene of interest may also be under the control of a regulatory element that itself is activated by a BNM3 protein. For example, which is not to be considered limiting, a gene of interest may be fused to the napin promoter, and the napin promoter may be induced by BNM3. Furthermore, a gene of interest may be expressed within somatic tissues under the control of one or more regulatory elements induced by BNM3, so that, as will be described in more detail below, the somatic tissue develops into a seed-like structure comprising embryogenic cells, and these seed-like structures produce the products of the gene of interest.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), fluorescence, or luminescence, such as luciferase are useful.

Also considered part of this invention are transgenic plants containing a gene or chimeric gene construct of the present invention comprising a BNM3 gene, a regulatory element obtained from BNM3, or the coding region from BNM3 in operative association with a constitutive, developmental or inducible regulatory element, or a combination thereof. Methods of regenerating whole plants from plant cells are known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. The constructs of the present invention can be introduced into plant cells using Ti plasmids, Ri plasmids, plant virus vectors, direct DNA transformation, micro-injection, electroporation, biolistics etc. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561–579 (1997). The present invention further includes a suitable vector comprising the gene or the chimeric gene construct.

A class of genes have been isolated from *Brassica napus* microspore embryo cultures. These genes have been found to be important regulators of embryogenesis by their ability to induce the formation of asexually-derived embryos when ectopically expressed in the vegetative tissues of plants. These genes are hereinafter indicated as BNM3 genes (*Brassica napus* microspore embryo). SEQ ID NO. 1 depicts the cDNA of BNM3A, SEQ ID NO. 3 depicts the cDNA of BNM3B, and the genomic sequence for BNM3A is given in SEQ ID NO:5. The regulatory region of BNM3A lies within nucleotides 1–1619 of SEQ ID NO:5. The predicted protein sequences encoded by the DNAs of SEQ ID NO. 1 and 3 are outlined in SEQ ID NOs. 2 and 4, respectively.

The orthologue of the BNM3 gene has also been identified in *arabidopsis* and is hereinafter referred to as AtBBM. SEQ ID NO:6 depicts the genomic sequence for AtBBM. The regulatory region of AtBBM lies within nucleotides 1–2025 of SEQ ID NO:6. The predicted amino acid sequence is given in SEQ ID NO:7.

The BNM3 translation products contain two copies of an AP2 domain separated by a linker region (FIG. 3; amino acids 208–378 of SEQ ID NO: 2, and SEQ ID NO: 4, nucleotides 2694–4252 of SEQ ID NO:5, nucleotides 2938–4416 of SEQ ID NO:6), which herein is referred to as "AP2domain" or "AP2 domain repeat1-linker-AP2domain repeat2". The AP2 domain is thought to mediate protein—protein interactions. The ability of a number of AP2 domain containing proteins to bind DNA, coupled with the presence of putative nuclear localization signals and acidic regions that may function as transcriptional activators suggests these proteins function as transcription factors. The AP2 domain repeat1-linker-AP2domain repeat2 of BNM3 exhibits about 99% homology with the AP2 domain of AtBBM (95% nucleotide similarity between BNM3 and AtBBM), as well as a high degree of similarity with other AP2-comprising proteins, for example, ANT about 85% (76% nucleotide similarity), MOE17 (chromosome 3) about 85% (78% nucleotide similarity; if the introns are included in the comparison, for example the AP2 region from SEQ ID NO5, then MOE17 exhibits about 63% nucleotide similarity over a 285 bp region within the second AP2 domain), ZMM-HCF1, 88%, or GLOSSY15, 66%. However, outside the two AP2 domains, the similarity of the sequence of BNM3 and these other AP2-containing proteins decreases significantly.

By "BNM3" or "BNM3 gene", it is meant the sequence of oligonucleotides as disclosed in SEQ ID NOs:1, 3, 5, or 6, or fragments, derivatives, or mutations thereof, or oligonucleotide sequences that exhibit at least:

i) 70% homology or similarity, with a fragment or derivative of the sequences disclosed in SEQ ID NOs 1, 3, 5 or 6, not including the AP2 domain repeat1-linker-AP2 domain repeat2 region as defined by nucleotides 741–1257 of SEQ ID NO:1 nucleotides 672–1188 of SEQ ID NO:3, the corresponding sequence within coding region of nucleotides 2694–4252 of SEQ ID NO:5, or nucleotides 2938–4416 of SEQ ID NO:6 (the regions defined by nucleotides 2694–4252 of SEQ ID NO:5 or nucleotides 2938–4416 of SEQ ID NO:6, are interrupted by 7 introns; see FIG. 9); or ii) 70% homology or similarity, with the full length of sequences disclosed in SEQ ID NOs 1, 3, 5 or 6 including the AP2 domain repeat1-linker-AP2 domain repeat2 region.

Such homology determinations may be made using oligonucleotide alignment algorithms for example, but not limited to a BLAST using default parameters: Program: blastn; Database: nr; Expect10; filter: default; Alignment: pairwise; Query genetic Codes: Standard (1)) or FASTA, again using default parameters. Using sequence similarity searches AtBBM exhibits about 85% homology with the full length of BNM3, and therefore, AtBBM is a BNM3 gene. Furthermore, a BNM3 gene may also be defined in terms of its ability to hybridize with sequences disclosed in the present invention. Therefore, "BNM3" or "BNM3 gene", also includes:

iii) oligonucleotides from greater than about 15 nucleotides in length, preferably 20 to 25 nucleotides in length, that associate with any of SEQ ID NO:1, 3, 5 or 6, or a fragment or derivative of the sequences disclosed in SEQ ID NOs 1, 3, 5 or 6, not including the region coding for the AP2 domain (AP2 domain repeat1-linker-AP2 domain repeat 2) as defined above, under conditions of high stringency, for example, but not to be limited to, hybridization using gel blots (Southern hybridization) at about 65° C. at 5×SSC, followed by wash conditions at 0.1×SSC, at 65° C.; or iv) substantially full length nucleotide sequences, or nucleotide sequences of greater than about 1000 nucleotides in length, that associate with SEQ ID NO:1, or 3, or a fragment or derivative of the sequences disclosed in SEQ ID NOs 1, 3 of a length greater than about 1000 nucleotides, not including the region coding for the AP2 domain (AP2 domain repeat1-linker-AP2 domain repeat 2) as defined above, under conditions of moderate or high stringency, for example, but not to be limited to, hybridization using gel blots (Southern hybridization) at about 25° C. at 0.2×SSC, 0.1% SDS, or 65° C. 5×SSC, respectively, followed by wash conditions at 0.2×SSC, 0.1% SDS at 25° C.

Under conditions of moderate stringency, the full length BNM3 cDNA only hybridizes with fragments of AtBBM (see FIG. 9B), and therefore, AtBBM is a BNM3 gene. Sequence analysis of the AtBBM genomic clones position the 5' end of the IRREGULAR XYLEM3 (IXR3) gene downstream of the putative AtBBM coding region (position 7479, FIG. 9A). IXR3 has previously been shown to map to a 150 kb region of chromosome 5 between the markers nga106 (33.26 cM) and mi438 (33.34 cM) (Taylor et al., 1999). This data indicates that the *arabidopsis* orthologue of the *Brassica* BNM3 genes is encoded by a single gene that maps to chromosome 5. A sequence highly similar to AtBBM, TAMU BAC clone:T10B6 (accession number AP002073; Nakamura, May 18, 2000) has also been mapped to chromosome 5.

"BNM3 gene" also includes DNA molecules that comprises at least 27 contiguous nucleotides of SEQ ID NOs:1, 3, 5, or 6 or at least 22 contiguous nucleotides within the regulatory region of nucleotides 1–1619 of SEQ ID NO:5, or nucleotides 1–2025 of SEQ ID NO:6. A fragment of BNM3, as defined may be used as a probe for the identification of nucleotides related to BNM3 regulatory, or coding, regions within an organism, or as primers for the amplification of these nucleotide sequences. Furthermore, molecules comprising at least 27 contiguous nucleotides, and preferably greater than about 30 to about 35 nucleotides, of the sequence of SEQ ID NOs:1, 3, 5 or 6 and that encode a protein, or an active fragment thereof, that when present at a sufficient level within a plant cell renders the cell embryogenic, increases the regenerative capacity of the plant cell, or renders the cell embryogenic and increases the regenerative capacity of the plant cell, are also considered to be BNM3 genes. Preferably, a BNM3 gene comprises from about 50 to about 1981 nucleotides of SEQ ID NOs: 1 or 3, from about 50 to about 3538 nucleotides from the coding region (1620–4858) of SEQ ID NO:5, or from about 50 to about 3009 nucleotides from the coding region (2025–5035) of SEQ ID NO: 6.

The genomic BNM3 sequences obtained from *Brassica napus* and *arabidopsis* are characterized as comprising 8 introns. These introns are found at nucleotides 1846–2298, 2720–2952, 3036–3160, 3170–3314, 3404–3553, 3628–3797, 3849–3961, and 4039–4148, of SEQ ID NO:5, and nucleotides 2249–2578, 2994–3220, 3304–3420, 3429–3521, 3611–3770, 3845–3969, 4020–4151 and 4229–4310 of SEQ ID NO:6. The start codon of SEQ ID NO's:5 and 6 are at nucleotides 1620 and 2026, respectively, while the stop codons are found at positions 4856 and 5035, respectively.

By "BNM3 regulatory region" it is meant the sequence of oligonucleotides that exhibit the property of regulating the expression of (either positively, for example an enhancer or promoter region, or negatively, for example a silencer region), and that are in operative association with, a BNM3 gene. Typically the BNM3 regulatory region comprises nucleotides upstream from the start site of a BNM3 gene, however, sequences residing within other regions of the gene may also exhibit regulatory properties and be considered a BNM3 regulatory region, for example but not limited to sequences within introns. An example of a BNM3 regulatory region, which is not to be considered limiting, includes:

a sequence operably linked with a BNM3 gene that exhibits a regulatory function, for example but not limited to a regulatory region upstream from the start site of a BNM3 gene or within an intron, or a fragment, derivative, or mutation thereof;

nucleotides from about 1 to about 1619 in SEQ ID NO:5 or a fragment or derivative thereof;

nucleotides from about 1 to about 2025 of SEQ ID NO:6 or a fragment or derivative thereof;

a nucleotide sequence that associates with a nucleotide sequence from about 1000 to about 1619 of SEQ ID NO:5 or from about 1500 to about 2025 of SEQ ID NO:6, or a fragment or derivative thereof, under conditions of high stringency, for example, but not to be limited to, hybridization to gel blots at about 65° C. in 5×SSC, followed by wash conditions at 0.1×SSC, 65° C.;

a nucleotide sequence that associates with a nucleotide sequence from about 1 to about 1000 of SEQ ID NO:5 or from about 1 to about 1500 of SEQ ID NO:6, or a fragment or derivative thereof, under conditions of moderate or high stringency, for example, but not to be limited to, hybridization to gel blots at about 25° C. in 0.2×SSC, 0.1% SDS, or 65° C. in 5×SSC, respectively, followed by wash conditions in 0.1×SSC, at 65° C.; or a nucleotide sequence that exhibits at least 70% similarity with the nucleotide sequence from about 1000 to about 1619 of SEQ ID NO:5 or from about 1500 to about 2025 of SEQ ID NO:6, or a fragment thereof of at least about 22 nucleotides, as determined using oligonucleotide alignment (for example, but not limited to a BLAST or FASTA search, using default parameters; see above).

By "BNM3 protein" it is meant a protein, or a biologically active fragment thereof, that renders a plant cell embryogenic, increases the regenerative capacity of the plant cell, or renders the cell embryogenic, increases the regenerative capacity of the plant cell, and that is encoded by a BNM3 gene, as defined above. Preferably, a BNM3 protein comprises from about 30 to about 579 amino acids of the sequence disclosed in SEQ ID NO:2, from about 30 to about 579 amino acids of the sequence disclosed in SEQ ID NO: 4, or from about 30 to about 581 amino acids of the sequence disclosed in SEQ ID NO:7. However, BNM3 protein may also be defined as a protein having at least 70% homology with either SEQ ID NO:2, 4, or 7 not including the AP2-repeat1-linker-AP2 repeat2 region (amino acids 208–378 of SEQ ID NO:s 2, and 3, amino acids 205–375 of SEQ ID NO:7).

Search of the sequence databases indicated that the BNM3 translation products contain two copies of an AP2 domain (FIG. 3; see also SEQ ID NO: 2 for BNM3A, SEQ ID NO: 4 for BNM3B, and SEQ ID NO:7 for AtBBM). The AP2 domain was first identified in APETALA2, an *arabidopsis* protein that regulates meristem identity, floral organ specification, seedcoat development and floral homeotic gene expression (Jofuku et al., 1994), but has since been identified in a wide range of proteins with diverse functions.

The AP2 domain is usually between 58 to 68 amino acids in length and contains a conserved central core of 18 amino acids, characterized by its ability to form an amphipathic α helix, a structure thought to mediate protein—protein interactions. The ability of a number of AP2 domain containing proteins to bind DNA, coupled with the presence of putative nuclear localization signals and acidic regions that may function as transcriptional activators suggests these proteins function as transcription factors.

Two phylogenetically distinct classes of AP2 domain proteins have been identified; proteins with a single AP2 domain (EREBP-like) and proteins with two AP2 domains (AP2-like; (Zhou, 1997)). The proteins encoded by the genes of this invention represent unique members of the latter class of proteins.

Accordingly, an aspect of the present invention provides for an isolated DNA molecule that comprises a sequence encoding a protein that contains two AP2 domains. The protein, when present at a sufficient level in a plant cell, renders the cell embryogenic, increases the regenerative capacity of the cell, or both renders the cell embryogenic and increases the regenerative capacity of the cell.

Figure 6:
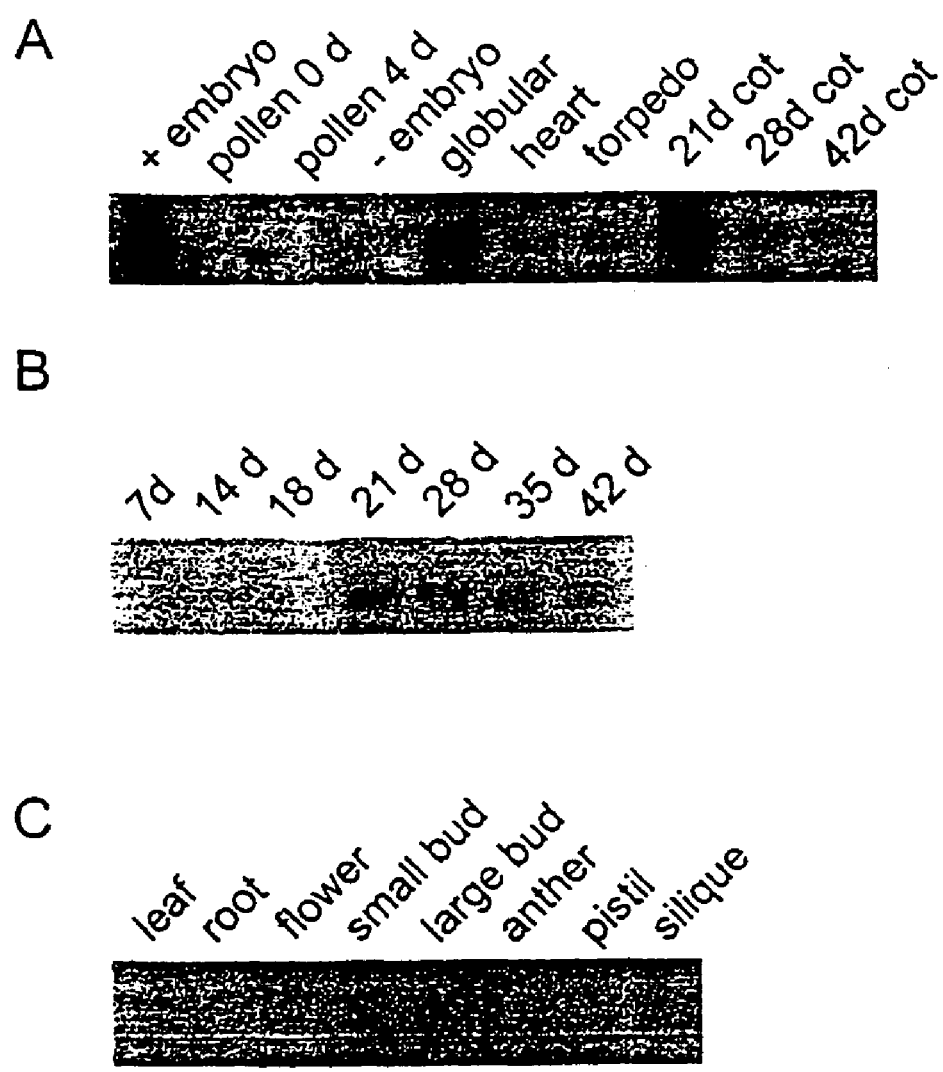
FIG. 6 shows the results of gel blot analysis with a BNM3A cDNA fragment performed on RNA extracted from the indicated tissues. RNA gel blots contain either 5 μg (a) or 20 μg (b, c) of total RNA.

Analysis of BNM3 expression during microspore-derived embryo development, seed development, or non-seed tissue development, using Northerns (FIG. 6) indicated that the BNM3 genes are preferentially expressed in embryogenic microspore cultures, microspore-derived embryos and seeds. BNM3 transcripts were not detected in any of the non-seed tissues tested.

BNM3 mRNA is detected in microspore cultures induced to undergo embryogenesis, as well as in the subsequent globular, heart, torpedo and cotyledon stages of microspore-derived embryo development (e.g. FIG. 6A). RNAs are also detected within developing seeds, 14 days after pollination (14 DAP), corresponding to the heart stage of embryo development. BNM3 expression increases during the early (21 DAP) and mid-cotyledon (28 DAP) stages of embryo development and remains constant thereafter (FIG. 6B).

Figure 7:
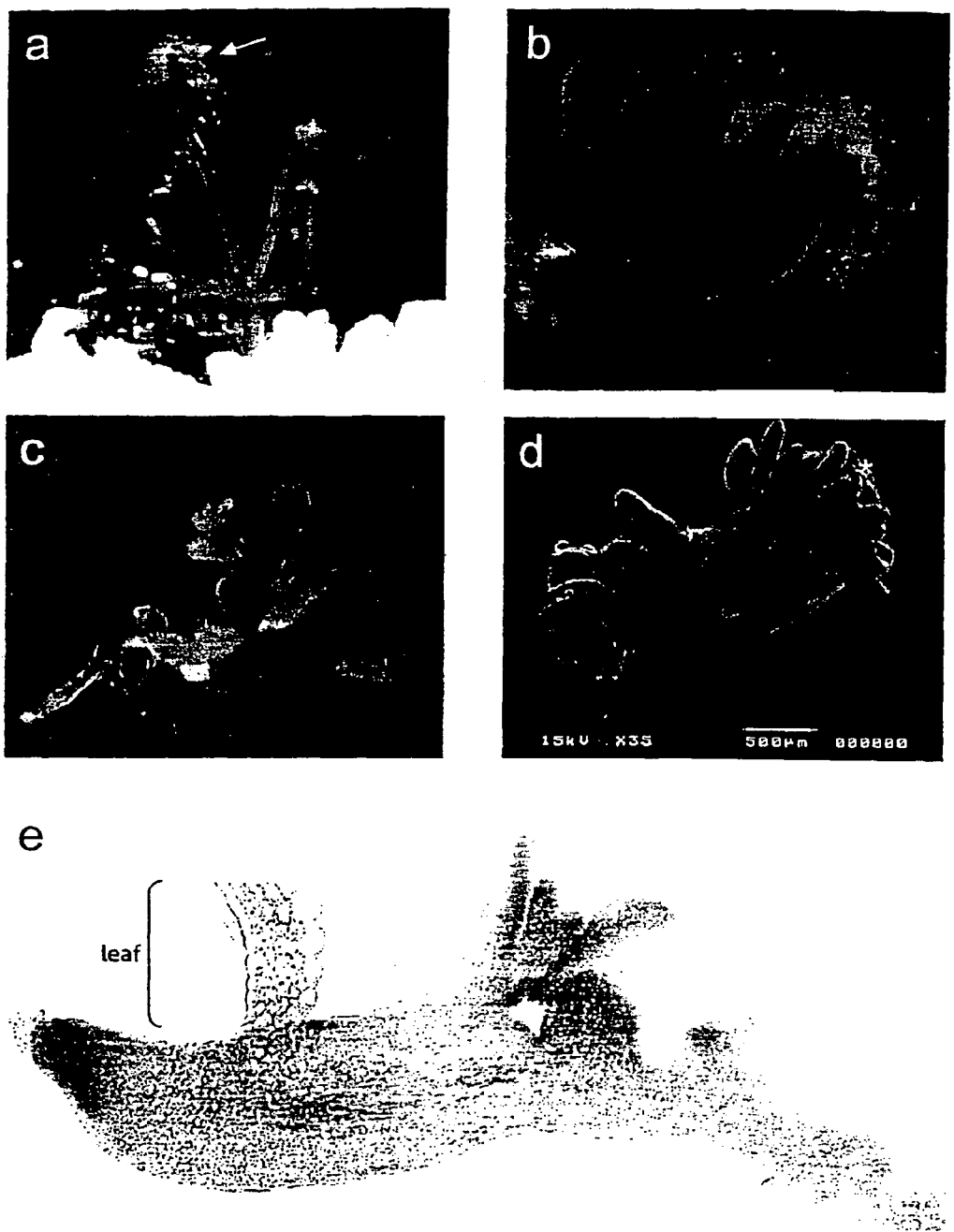
FIG. 7 shows the phenotype of *Brassica napus* and *arabidopsis* plants transformed with constructs containing the BNM3 gene under control of a modified POLYUBIQ-UITIN promoter (B) and double enhanced 35S promoter containing an AMV translational enhancer (A, C-E).

Constitutive expression of BNM3 resulted in the formation of somatic embryos on vegetative structures such as cotyledons, petioles, leaf blades and the shoot apical meristem of plants (FIG. 7). In these experiments BNM3 cDNAs were placed under the control of two separate constitutive promoter constructs, a modified sunflower POLYUBIQUITIN promoter construct, and a double enhanced 35S promoter construct containing an AMV translational enhancer, however, it is to be understood that any suitable constitutive promoter may be used for this purpose. Such BNM3-derived ectopic embryos contain all of the organ systems and tissue layers found in the developing zygotic embryo in that these embryos are bipolar (FIG. 7E), consist of an axis, a hypocotyl and radicle region, shoot and root meristems, and cotyledons. In addition, each organ system contained the characteristic radial arrangement of three specialized tissue layers (epidermis, ground parenchyma and provascular tissue) found in zygotic embryos. Continued expression of the BNM3 gene within the developing ectopic embryo leads to a reiteration of the embryo-forming process, with the result that new embryos are continuously formed on the surface of pre-existing embryos (FIG. 7E).

Figure 8:
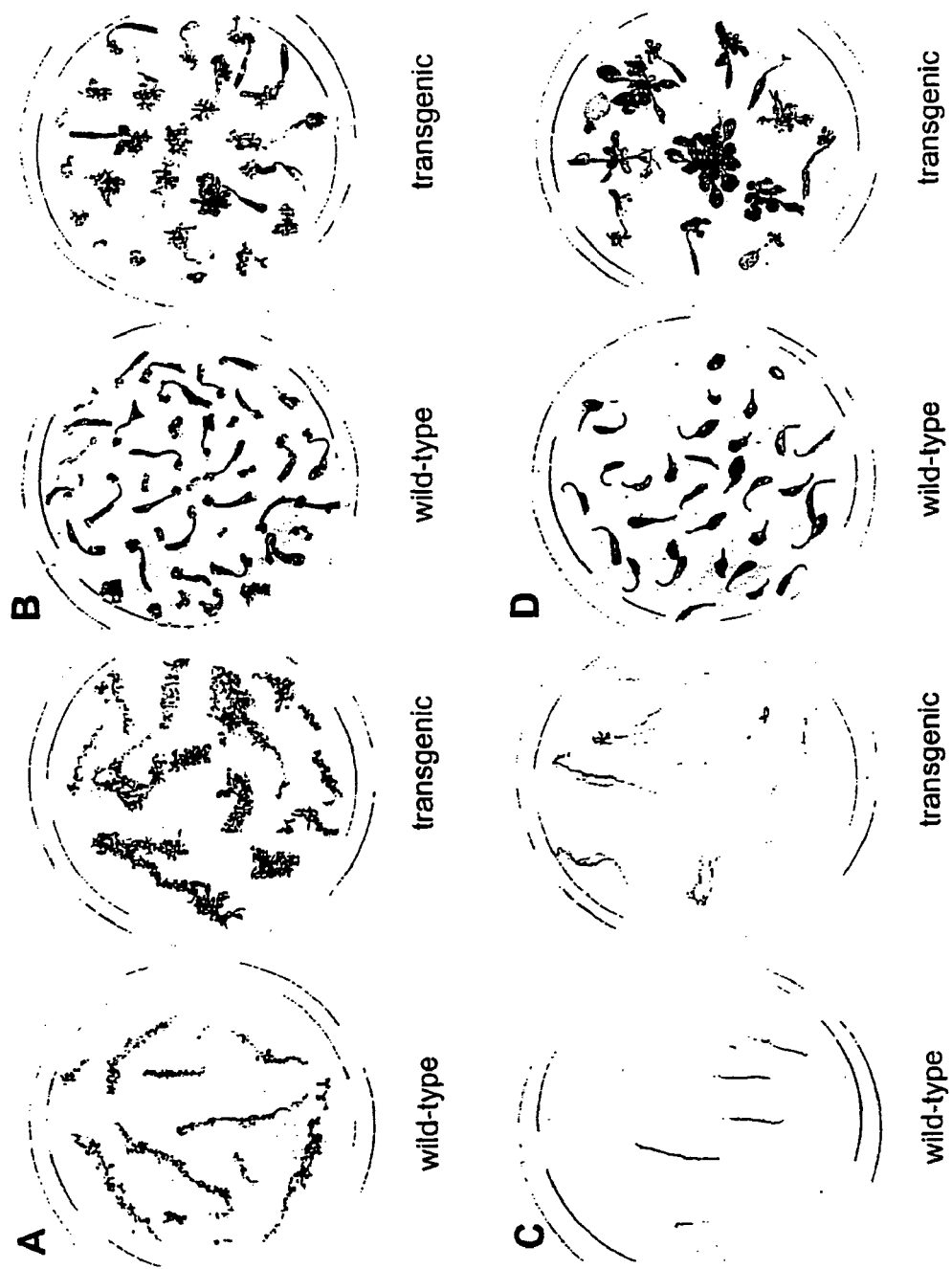
FIG. 8 shows the increased regenerative capacity of *arabidopsis* plants transformed with a construct containing the BNM3B gene under control of a modified POLYUBIQ-UITIN promoter.

Constitutive expression of BNM3 results in the increased ability of a plant to regenerate shoots in vitro in the presence of added growth regulators. Root explants from transgenic plants ectopically expressing BNM3 show at least a 5-fold increase in shoot regeneration in the presence of hormones as compared to root explants obtained from wild-type plants (FIGS. 8A,B). Shoots also developed faster in the transgenic explants, compared to the wild-type. Wild-type leaf and hypocotyl explants initially responded by producing callus on the cut end of the petiole (FIG. 8B) followed by callus formation along the length of the petiole. In contrast, explants from transgenic lines immediately produced new shoots (FIG. 8B) or roots from the cut end of the petiole. Explants that initially produced roots eventually also produced shoots.

Transgenic explants, constitutively expressing BNM3 were also able to regenerate in the absence of added growth regulators. These explants, when placed on media lacking growth regulators regenerated shoots either from the cut end of the leaf and hypocotyl explants or from the nodule-like structures of root explants (FIGS. 8C,D). In all cases regenerated shoots developed, rooted, flowered and set seed. Conversely, wild-type leaf and hypocotyl explants placed on medium lacking growth regulators occasionally produce callus or roots at the cut end of the leaf petiole, however no shoots form from these structures (FIGS. 8C,D).

It is also considered within the scope of the present invention, that expression of BNM3 may be used to initiate a developmental cascade within a transformed plant or plant cell. This cascade may arise as a result of the stable integration of a DNA-based vector expressing BNM3 within a transformed plant, however, such a cascade may also arise as a result of transient expression of BNM3, and does not require the stable integration of the BNM3-based vector within a plant cell. These transient approaches may be useful for inducing somatic embryogenesis, gametophytically-derived embryogenesis, or increasing the regenerative capacity of a plant or plant cell.

Plants in which a BNM3 gene is ectopically expressed exhibit advantageous qualities including:
formation of asexually derived embryos;
increased regenerative capacity of tissue explants;
the ability of tissue explants to regenerate in the absence of added plant growth regulators; and
the expression of seed components in non-seed organs in which BNM3 is ectopically expressed.

Furthermore, plants that ectopically express at least one BNM3 gene can be used for the production of recombinant proteins using seed specific regulatory elements.

For the applications of BNM3 as described below, it will be advantageous to obtain a high level of the BNM3 transcript and/or BNM3 protein in order to obtain plants in which the phenotype is highly penetrant. This may be obtained by using genetic elements such as introns, transcriptional enhancers or translational enhancers which are known to enhance gene or protein expression levels.

The BNM3 sequences of the present invention may be used for several applications including, but not limited to, the control of embryo processes, the control of regeneration processes, the use of regulatory sequences for targeted gene expression, the use of BNM3 sequences as selectable markers of transformed plants, or for embryogenic cells. These applications are disclosed in more detail below.

Use of BNM3 Sequences to Control Embryogenic Processes

As described herein, BNM3 genes play an important role in initiation and maintenance of embryo development. BNM3 genes have been found in a wide range of members of the plant kingdom. Regulatory regions obtained from these genes may be used to control the transcription of BNM3 or a derivative or fragment thereof, or any gene of interest, using methods known to one of skill in the art.

Ectopic expression of a BNM3 gene is sufficient to induce recurrent formation of asexually derived embryos on the vegetative tissues of plants (see example 4). Depending upon the promoter used, ectopic over-expression of BNM3 genes may be used to produce somatic or gametophytic embryos. Somatic or gametophytic embryos may be obtained by expressing a BNM3 gene under the control of a constitutive regulatory element, as is shown in Example 5, or may also be obtained by expressing a BNM3 gene under the control of tissue specific or developmentally regulated elements, inducible elements derived from either plant or non-plant genes or through transient expression. In this respect, chemical induction systems (e.g. see Gatz and Lenk, 1998, which is incorporated by reference) or transient expression using methods which do not result in stable integration of the BNM3 gene, or which make direct use of the BNM3 protein e.g. microprojectile bombardment of DNA or protein may also be employed.

Temporal and/or spatial restriction of BNM3 expression using inducible, tissue specific or developmentally regulated elements, is preferred when recurrent embryogenesis is not a desirable trait. The regulatory elements used to restrict BNM3 to a specific developmental stage or cell type will depend on the application. For example, regulatory elements that may be used to express BNM3 for the production of microspore-derived embryos include, but are not limited to, those of the class I low molecular weight heat shock inducible gene, GMHSP 17.3B (Zarsky et al., 1995, which is incorporated by reference), or microspore/pollen expressed genes such as NTM19 (Custers et al., 1997, EP 790,311, which are incorporated by reference), BCP1 (Xu et al., 1995, which is incorporated by reference), LAT52 (Twell et al., 1989, which is incorporated by reference), BNM1 (Treacy et al 1997, which is incorporated by reference) and APG (Roberts et al., 1993, which is incorporated by reference).

Examples of regulatory elements that may be used to express BNM3 for the production of somatic embryos include, but are not limited to, those of genes activated by plant growth regulators which are routinely used to induce somatic embryogenesis in tissue culture. Specific examples, which are to be considered non-limiting, include the cytokinin inducible IB6 and CKI1 genes (Brandstatter and Kieber, 1998; Kakimoto, 1996, which are incorporated by reference) and the auxin inducible element, DR5 (Ulmasov et al., 1997, which is incorporated by reference). However, it is to be understood that other regulatory elements may be included for the expression of BNM3 in plants.

Furthermore, examples of gene regulatory elements suitable for directing expression of BNM3 to obtain adventitious embryony include, but are not limited to, those obtained from the ovule and embryo expressed SERK gene (Schmidt et al, 1997 which is incorporated by reference), the ovule expressed AGL11 gene (Roundsley et al., 1995, which is incorporated by reference), the nucellus expressed NUC1 gene (Doan et al., 1996; WO 98/08961, which are incorporated by reference), or the inner integument-expressed genes, FBP7 (Angenent et al, 1995, which is incorporated by reference) and SC4 (U.S. application Ser. No. 09/059,909, filed Apr. 13, 1998, which is incorporated by reference) genes.

According to one aspect of the present invention there is provided a method for the efficient production of microspore-derived embryos in plants. This method involves:

i) transforming a plant of interest, for example, *Brassica napus* (using transformation techniques known to one of skill, for example, DeBlock et al., 1989, Clough and Bent 1998, Vergunst et al. 1998, Klein et al 1987, which are incorporated herein by reference) with a vector construct, or isolated DNA, consisting of a BNM3 gene under control of a suitable regulatory element, which may be constitutive, tissue specific, developmentally regulated, or inducible and, optionally, a marker gene for selection of transformants;

ii) selecting transformed plants;

iii) producing lines that ectopically overexpress the BNM3 gene, or BNM3 protein;

iv) isolating microspores and pollen from the transgenic lines and culturing microspores and pollen to induce embryogenesis.

Embryogenesis can be induced by any suitable protocol, for example, which is not to be considered limiting, culturing microspore and pollen for about four days at from about 28° to about 35° C., preferably at about 32° C., then transferring embryogenic cells or embryos to about 25° C.

Using the above method, *Brassica napus* cultivars ectopically overexpressing BNM3 show an increase in the percentage of embryogenic cells or embryos over that observed when microspores or pollen are prepared from wild-type plants that do not ectopically express BNM3.

Examples of regulatory elements that may be used to express BNM3 for the production of microspore-derived embryos include, but are not limited to, those of the class I low molecular weight heat shock inducible gene, GMHSP 17.3B (Zarsky et al., 1995, which is incorporated by reference), or microspore/pollen expressed genes such as NTM19 (Oldenhof et al., 1996, EP 790,311, which are incorporated by reference), BCP1 (Xu et al., 1995, which is incorporated by reference), LAT52 (Twell et al., 1989, which is incorporated by reference), BNM1 (Treacy et al 1997, which is incorporated by reference), and APG (Roberts et al., 1993, which is incorporated by reference). Also useful are inducible regulatory elements, for example but not limited to, tetracycline-inducible promoter (Gatz 1997, which is incorporated by reference), steroid inducible promoter (Aoyama and Chua 1997, which is incorporated by reference) and ethanol-inducible promoter (Slater et al 1998, Caddick et al. 1998, which are incorporated by reference).

In a similar fashion, microspore-derived embryos may also be produced in plants by introducing into a plant of interest a BNM3 protein, (e.g. via biolistics; Klein et al 1987) and selecting for plants that exhibit increased microspore embryogenesis.

This invention also provides a method for the efficient production of somatic embryos in vitro. This method involves:

i) transforming a plant, for example, *arabidopsis* using transformation techniques known to one of skill (for example, but not limited to, DeBlock et al., 1989, Clough and Bent 1998, Vergunst et al. 1998, which are incorporated by reference), or a plant cell may also be transiently transformed using methods known to one of skill (for example, biolistics; Klein et al 1987) with a vector construct containing a BNM3 gene under control of suitable regulatory element, which may be constitutive, inducible or developmentally regulated, and, optionally, a marker gene for selection of transformants is transformed to several *arabidopsis*.

ii) selecting transformed plants, and iii) culturing the desired explant from the selected transformed plants, for example, but not limited to, root, leaf or seedlings in vitro, in media with or without appropriate growth regulators, for example, but not limited to 2,4-D (e.g. Mordhorst et al., 1998) to produce direct embryogenesis or embryogenic callus; and iv) transferring embryos, non-embryogenic callus, or both embryos and non-embryogenic callus to appropriate media for the production of embryos, plantlets, or both embryos or plantlets.

For example, when the results of the above method are compared with the production of somatic embryos in vitro using a number of *arabidopsis* ecotypes, directed embryogenesis or embryogenic callus is initiated at a higher frequency from transgenic lines ectopically over-expressing BNM3 than in wild-type controls.

Examples of regulatory elements that may be used to express BNM3 for the production of somatic embryos include, but are not limited to, those of genes activated by plant growth regulators which are routinely used to induce somatic embryogenesis in tissue culture. Specific examples, which are to be considered non-limiting, cytokinin inducible IB6 and CKI1 genes (Brandstatter and Kieber, 1998; Kakimoto, 1996, which are incorporated by reference) and the auxin inducible element, DR5 (Ulmasov et al., 1997, which is incorporated by reference). Also useful are inducible regulatory elements, for example but not limited to, a tetracycline-inducible promoter (Gatz 1997, which is incorporated by reference), a steroid inducible promoter (Aoyama and Chua 1997, which is incorporated by reference), and an ethanol-inducible promoter (Slater et al 1998, Caddick et al. 1998, which are incorporated by reference).

Ectopic initiation of embryo development is one of the key steps in apomixis. As shown in Example 4, ectopic expression of a BNM3 gene is sufficient to initiate embryo formation in otherwise non-embryo-forming tissue. A BNM3 gene may therefore be used to initiate adventitious embryony or parthenogenesis of a reduced or unreduced embryo sac cell by expression of the gene in the sporophytic or gametophytic tissues of the developing ovule.

Adventitious embryony is achieved by expressing BNM3 in sporophytic ovule tissues such as the nucellus, the inner integuments or other tissues lying adjacent to or in proximity to the developing embryo sac. This method involves:
i) transforming a desired plant (see above methods) with a vector construct consisting of a BNM3 gene under control of suitable regulatory element, which may be constitutive, inducible or developmentally regulated, and, optionally, a marker gene for selection of transformants, using methods known within the art;
ii) selecting transformed plants;
iii) emasculating the transformed plant;
iv) pollinating the transformed plants with pollen carrying one or more dominant selectable markers, for example GUS or kanamycin resistance; and
v) assaying for production of clonal offspring.

When the results of the above method are compared with the pollination of a wild-type arabidopsis plant with pollen carrying the dominant selectable marker, all F1 embryos resulting from this cross inherit the dominant marker while embryos derived from plants ectopically over expressing the BNM3 gene or protein are clonally derived via sexual embryo formation and do not inherit the dominant selectable marker.

Specific examples of gene regulatory elements suitable for directing expression of BNM3 to obtain adventitious embryony, diplospory or haploid parthenogenesis of embryo sac components include the ovule expressed SERK gene (Schmidt et al. 1997, which is incorporated by reference), the meiosis expressed AtDMC1 gene, (Klimyuk and Jones, 1997; WO 98/28431, which are incorporated by reference), the ovule expressed AGL11 gene (Roundsley et al., 1995, which is incorporated by reference), the nucellus expressed NUC1 gene (Doan et al., 1996; WO 98/08961, which are incorporated by reference), and the inner integument-expressed genes, FBP7 (Angenent et al, 1995, which is incorporated by reference) and SC4 (U.S. application Ser. No. 09/059,909, filed Apr. 13, 1998, which is incorporated by reference) genes. Furthermore, inducible systems, for example but not limited to, tetracycline-inducible promoter (Gatz 1997, which is incorporated by reference), steroid inducible promoter (Aoyama and Chua 1997, which is incorporated by reference), ethanol-inducible promoter (Slater et al 1998, Caddick et al. 1998, which are incorporated by reference) may also be used. Parthenogenesis from cells of the embryo sac requires a regulatory element that is active in one or more cells of the female gametophyte or their precursors. Fertilization of the meiotically-derived polar nuclei is desirable when the development of seed is dependent on the presence of endosperm.

Use of BNM3 Sequences to Control Regeneration Processes

Plants ectopically over-expressing the BNM3 genes exhibit increased regenerative capacity and the ability to regenerate whole plants in the absence of added growth regulators (see example 5). BNM3 gene expression may therefore be used to enhance or induce the regeneration capacity of plant tissues in vivo or in vitro. The regulatory elements used to express BNM3 will depend, in part, on the target tissue used for regeneration. Regeneration of plant tissues may be obtained by expressing a BNM3 gene under the control of a constitutive regulatory element, for example, but not limited to, 35S, or by expressing a BNM3 gene under the control of tissue specific or developmentally regulated elements, inducible elements derived from either plant or non-plant genes (e.g. Gatz and Lenk, 1998, which is incorporated by reference), or through transient expression methods which do not result in stable integration of the BNM3 gene or which make direct use of the BNM3 protein (e.g. microprojectile bombardment of DNA or protein). Chemical induction systems (see Gatz and Lenk, 1998) or regulatory elements of genes that respond to plant growth regulators used to induce regeneration, such as, for example, cytokinin (Brandstatter and Kieber, 1998; Kakimoto, 1996) or auxin (Ulmasov et al., 1997), or genes expressed at the wound site of tissue explants (Xu et al., 1993) may be used.

A further application is the use of a BNM3 gene as a selectable marker for the recovery of transgenic plants. As an example of this application which is not to be considered limiting in any manner, roots of a seedling, for example, an Arabidopsis ecotype C24 seedling, are cocultivated with a single Agrobacterium tumefaciens strain (per Vergunst et al, 1998; except that all steps are carried out in the absence of added growth regulators) containing two binary constructs:
a first binary vector carries a reporter gene fusion, for example, but not limited to, 35S:GUS;
a second binary vector contains a BNM3 gene under control of suitable regulatory element.

BNM3 gene expression is activated upon integration of the above construct into the arabidopsis genome and transgenic plants are selected on the basis of their ability to regenerate under conditions in which wild-type explants are unable to regenerate, for example, but not limited to, the absence of growth regulators. In many instances the T-DNA carrying the BNM3 gene and the T-DNA carrying the gene of interest will integrate at unlinked loci. The T-DNA containing the introduced BNM3 sequence, and it's associated increased regenerative capacity phenotype, may therefore be removed in the progeny plants by simple segregation (Daley et al. 1998). However, as will be apparent to one of skill in the art, other methods such as transient expression, which do not result in stable integration of the BNM3 gene or which make direct use of the BNM3 protein, may also be employed.

Use of BNM3 Sequences to Target Gene Expression to the Embryo

Since BNM3 genes are preferentially expressed in developing embryos (see example 3), a further application of this invention is the use of BNM3 regulatory regions to target expression of at least one heterologous gene of interest to the developing embryo for any purpose, for example, but not limited to, altering embryo and seed traits such as seed viability or size, composition of constituents of the seed, disease resistance, or the production of high value products such as vaccines antibodies, biopharmaceuticals or other specialty chemicals.

Use of BNM3 Expression as a Marker for Embryogenic Cells

As shown in Examples 3 and 4, BNM3 gene expression is detected during the earliest phase of plant embryogenesis and is itself sufficient to activate signal transduction cascades leading to embryo development. BNM3 gene expression is therefore a specific marker for the entry of a plant cell into the embryogenic pathway.

BNM3 expression is associated with embryo-forming cell divisions in vitro and in vivo and as such can be used to define culture conditions that alter the embryo-forming capacity of a tissue in vitro. Cells with embryogenic capacity or cells that undergo only a limited number of embryo-forming divisions are difficult to identify in the absence of structures that morphologically resemble embryos. However, these cells may be identified on the basis of BNM3 expression. In this application, a vector containing the BNM3 regulatory region, fused to a reporter gene, for example, but limited to, GUS (Jefferson et al., 1987), Luciferase (Ow et al., 1987) or GFP (Haselhoff and Amos, 1995) is transformed to a plant of interest. Homozygous transgenic lines exhibiting high levels of reporter gene expression in the embryo are cultured under in vitro conditions. Embryogenic cells, as well as culture conditions which facilitate or enhance the formation of embryogenic cells are identified on the basis of reporter gene expression within the cultured tissue.

A related application is the use of the BNM3 gene as a marker in apomictic species for the identification of individual cells that are in the process of forming asexually-derived embryos. In this application, cells entering the autonomous embryo pathway are identified by mRNA in situ hybridization using a RNA probe derived from a BNM3 gene sequence, by immunocytochemistry using a antibody directed against a BNM3 protein, by transforming plants with a DNA construct containing a gene fusion between BNM3 regulatory regions and a reporter gene, or by any similar technique known to those skilled in the art.

Identification of Signal Transduction Components

Signal transduction components which activate or are activated by BNM3 gene expression can be elucidated by identifying proteins and DNA sequences that interact with a BNM3 gene and its protein product. These signal transduction components may be identified using techniques known to a person skilled in the art, including for example, but not limited to:

mutagenesis to identify intr- and/or extragenic suppressors or enhancers of the BNM3 gain-of-function phenotype;

yeast one hybrid screens for the isolation of proteins that bind to the BNM3 regulatory regions to influence BNM3 gene expression;

genetic selection in yeast to identify genes that are direct targets of BNM3 binding;

DNA arrays or proteomics to identify genes which are activated in a BNM3 signal transduction cascade; and yeast two hybrid screens to identify proteins that interact with BNM3 to influence expression of downstream target genes.

Techniques for the analysis of the signal transduction components and signalling components are well known (see for example, Meijer et al. (1998), Lipshutz et al. (1999), and Anderson and Anderson (1998)).

Plants over-expressing the BNM3 gene under control of a strong constitutive regulatory element such as, for example, but not limited to, the Cauliflower Mosaic Virus 35S promoter exhibit ectopic embryo formation, enhanced regeneration via organogenesis or a combination thereof (Examples 4 and 5). The ability of BNM3 ectopic over-expression to induce both embryo formation and enhance regeneration processes can be used to identify mutants altered in their embryo-forming or regenerative capacity. In this application a vector construct consisting of a BNM3 protein coding region under control of a regulatory element that is sufficient to promote either ectopic embryo formation or enhanced regeneration phenotype is made and introduced into a plant of interest. Homozygous transgenic lines exhibiting a high penetrance of ectopic embryo formation, enhanced regeneration phenotype, or a combination thereof are identified. These lines are mutagenized by any available technique well known to the person skilled in the art, but which may include EMS mutagenesis, fast neutron mutagenesis, transposon mutagenesis or T-DNA mutagenesis. Mutagenized plants are then screened for alterations in the ectopic embryo formation or regeneration phenotype. These alterations include, for example, but not limited to, elimination or enhancement of the ability to promote ectopic asexual embryo formation or to regenerate in the absence of added growth regulators.

Heterologous Protein Expression System

Genetic control of the signal transduction pathway leading to embryogenesis and organogenesis in non-seed organs of transgenic plants may be activated by ectopic expression of a BNM3 gene. Expression of a BNM3 gene in association with a heterologous promoter can be used to produce altered seed components including for example, proteins, oils and other metabolites. Biotransformation of desired organs may also include altering the nutritive value of, for example leaves of forage crops, or it may be used to create alternative uses for crops. The use of promoters that are induced by the signal transduction cascade initiated by expression of BNM3 can be used to express high-valued recombinant proteins in organs other than seeds. An example of one such promoter is the napin promoter, obtained from the 2S seed storage protein napin. The production of proteins initiated from a BNM3-induced cascade, may be achieved within organs exhibiting greater biomass than seeds. Therefore, this technology may be used to create alternatives for plants as crops.

Accordingly, the present invention further relates to a binary system in which the BNM3 protein binds directly or indirectly to an embryo-expressed regulatory sequence (target sequence) and activate transcription of a chimeric gene construct in any plant cell, tissue or organ. Therefore, BNM3 may be used to directly or indirectly activate transcription of a chimeric gene construct. This approach involves BNM3 interacting either directly with at least one target sequence from an embryo-expressed gene, or indirectly by initiating an embryogenic signal cascade that activates a transcription factor that in turn binds to and activates transcription from at least one target sequence. This binary system may be used for the expression of proteins in somatic tissues with the properties of expression in seeds.

In this application transgenic plants containing the BNM3 gene under control of a constitutive regulatory element, for example, but not limited to the 35S promoter (35S:BNM3) are created to produce a BNM3 activator line. BNM3 expression may be demonstrated in a wide range of tissues in the BNM3 activator lines by RNA gel blot analysis. Stable homozygous activator lines with high levels of BNM3 expression are identified. Somatic tissues over-expressing BNM3 may be examined for expression of other embryo-expressed genes, such as arabin (Guerche et al., 1990), cruciferin (Pang et al., 1988) or oleosin, or for morphological properties that are normally characteristic of seeds, such as the presence of lipid or protein bodies.

Transgenic plants of the same species to that used to generate the BNM3 activator lines described above are also created which contain an embryo-expressed promoter fused to a gene of interest, to produce a gene of interest line. In order to help describe this embodiment, the gene of interest line expresses a reporter gene, such as GUS, and examples, which are not to be considered limiting, of such lines include *Brassica napus* 2S albumin seed storage protein gene, BngNAP1: GUS fusion (Baszczynski et al., 1994) or a SERK:GUS fusion (Schmidt et al., 1997; a non-seed expressed reporter construct such as BNM1:GUS (Treacy et al., 1997) may be used as a negative control). The fidelity of expression of the gene of interest in the specific organs and tissues of these gene of interest lines is demonstrated for each construct. Stable homozygous lines with high levels of expression of the gene of interest expression are created.

Transgenic lines containing BNM3 activator lines and gene of interest lines are crossed and the progeny seeds collected. BNM3 gene expression, and in this example, GUS activity, expression of other embryo-expressed genes, as well as the morphological characteristics of transformed tissues, are examined. BNM3 expression in non-seed tissues typically activates both embryo development and expression of the gene of interest (e.g. GUS), however, activation of the expression of the gene of interest in the absence of morphologically discernible embryos may also be observed. Expression of the gene of interest, in the absence of morphologically discernible embryos provides initial evidence for direct interaction of BNM3 with the target sequence.

Direct interaction of BNM3 with a target sequence may also be demonstrated using transient expression of BNM3 in plant protoplasts, along with the transient co-expression of an embryo-expressed promoter fused to a gene of interest (i.e. a gene of interest construct). 35S:BNM3 DNA and the gene of interest construct are introduced into protoplasts derived from non-seed cells, such as leaf mesophyll cells by electroporation. The expression of the gene of interest is examined after several hours to confirm activation of the target sequence. Direct interaction of BNM3 with the target sequence may further be demonstrated by co-introducing the target sequence alone as competitor DNA.

In order to determine if tissues from different plant species may be transactivated by BNM3, 35S:BNM3 DNA and a reporter gene (for example, but not limited to GUS) construct may be introduced by microprojectile bombardment into somatic tissues of a plant. If BNM3 interacts directly with a target sequence then expression of the report er gene should coincide with transient expression of BNM3 in all species and tissues.

Direct evidence for BNM3-target sequence interaction may also be obtained by isolation of BNM3 protein expressed in bacteria, insect or yeast. BNM3 is expressed in bacteria, insect, or yeast using commercially available expression systems and isolated to purity. Gel mobility shift assays (Gustavson et al., 1991) are performed using a BNM3-target sequence, for example an embryo-expressed target sequence, to demonstrate direct binding of BNM3 to the BNM3-target sequence. Footprint analyses may also be performed to locate the region of BNM3 binding. Fragments of target sequences that bind BNM3 may then be subcloned and used as competitors for BNM3 binding in transient assays described above.

The following description is of a preferred embodiment by way of example only and without limitation to the combination of features necessary for carrying the invention into effect.

The present invention will be further illustrated in the following examples. However it is to be understood that these examples are for illustrative purposes only, and should not be used to limit the scope of the present invention in any manner.

EXAMPLES

General Methods: Microspore Embryo Culture

*Brassica napus* c.v. Topas was used as the source of all plant material for microspore embryo culture. Donor plants for microspore culture were grown in a growth cabinet at 20° C./15° C. (day/night) with a 16 h photoperiod (400 µE/m/s) provided by VHO cool white fluorescent lamps (165 W, Sylvania) and incandescent bulbs (40 W, Duro-test). Four weeks after germination the plants were transferred to growth cabinets under the same light conditions, but set at 10° C./5° C. (day/night). Microspores and pollen were isolated and cultured as described in Keller et al. (1987), except that after 21 days in culture, cotyledon stage embryos were transferred to a maturation medium consisting of ½×NLN salts, 1% sucrose, 0.35 M mannitol and 5 µM ABA. Uninduced cultures (microspores and pollen continuing gametophytic development) and heat-stressed, non-embryogenic cultures (used for construction of the subtracted probe), were cultured from the same starting material as was used for the initiation of embryogenic cultures. Uninduced samples were obtained by culturing microspores and pollen for four days at 25° C. Heat-stressed, non-embryogenic samples were obtained by culturing microspores and pollen for one day 25° C., followed by three days 32° C.

Samples of microspore and pollen cultured for less than 10 days were collected by centrifugation. Older samples containing globular, heart, torpedo and cotyledon stage microspore-derived embryos were collected by filtration through nylon meshes of various pore sizes as described in Ouellet et al. (1992). All other plant tissues were collected from greenhouse grown material. Seed material was obtained by hand pollinating flowers on the day of anthesis and collecting developing seeds on various days after pollination (DAP).

Nucleic Acid Isolation and Analysis

Total RNA was isolated using either a cesium chloride/guanidinium isothiocyanate procedure (Ouellet, 1992) or TRIZOL reagent (Gibco-BRL). RNA gel blot analysis was carried out by separation of 5 to 20 µg of total RNA per lane through 1.5% agarose gels containing 0.62 M formaldehyde, essentially as in Sambrook et al. (1989), followed by capillary transfer to Hybond-N nylon membranes (Amersham). Poly(A)$^+$ RNA was isolated from total RNA by oligo (dT)-cellulose chromatography (Sambrook,1989).

Genomic DNA was isolated from leaf tissue as described in Fobert et al. (1991) and digested with the specified restriction enzymes using standard procedures (Sambrook, 1989). DNA gel blot analysis was carried out by electrophoresis of 10 µg DNA through 0.8% agarose gels followed by capillary transfer to Hybond-N membranes.

The partial 1.2 kb BNM3A cDNA insert was used as a probe for DNA and RNA gel blots. Hybridization to gel blots was carried out at 65° C. according to the Hybond-N protocol. The final wash conditions were 0.1×SSC, 65°.

Subtractive Probe Construction and cDNA Library Screening

Poly (A) mRNA was isolated from late uninucleate microspores and early binucleate pollen that had been cultured for four days at 32° C. in order to induce embryogenesis (embryogenic sample) and used to synthesize first strand cDNA (Riboclone cDNA kit; Promega). The cDNA was then hybridized to a five-fold excess (by weight) of poly (A)$^+$ RNA from late uninucleate microspores and early binucleate pollen that had been cultured for one day at 25° C., followed by three days at 32° C. to inactivate embryogenesis (non-embryogenic sample: Pechan et al., 1991). The subtractive hybridization was performed essentially as described in Sambrook et al. (1989). The single-stranded cDNA recovered after subtraction was labelled with [α-$^{32}$P] dCTP using a random primers kit (BRL) and used as the subtracted probe for screening a Lambda phage cDNA library constructed from the same embryogenic sample described above (Boutilier, 1994). Triplicate nylon filter lifts (Hybond-N) from approximately 1.5×10$^5$ plaque-forming units of the library were screened with the subtracted probe, with a random primers-labelled first strand non-embryogenic probe and with a random primers-labelled napin seed storage protein cDNA probe (pN2; (Crouch, 1983). Napin mRNAs are prevalent in the embryogenic microspore library (Boutilier, 1994) and therefore plaques hybridizing to the napin probe were removed from the subsequent screening steps. Plaques hybridizing to the subtracted probe, but not to the non-embryogenic or napin probes, were selected and subjected to two subsequent rounds of differential screening using both the subtracted and non-embryogenic cDNA probes. DNA from selected Lambda clones was isolated (Sambrook, 1989), partially digested with Eco RI and Xba I and subcloned into pGEM-4Z (Promega).

Seven cDNAs comprising 6 unique genes, one of which comprised a truncated BNM3A cDNA, were identified. Two distinct, full length BNM3 cDNA clones (BNM3A and BNM3B) were subsequently obtained by stringent screening of circa 2.5×10$^5$ plaque-forming units of a cDNA library (UniZAPII cDNA synthesis kit, Stratagene) constructed with mRNA from 10 day old globular to heart-stage microspore-derived embryos of *B. napus* c.v. Topas. The BNM3 cDNA inserts were rescued by in vivo excision into Blueskript SK(−) (Stratagene).

Isolation of *Brassica Napus* Genomic DNA Sequences

The Universal Genome Walker Kit (Clonetech) was used to isolate genomic DNA fragments lying upstream of the BNM3 ATG start codon. Pools of uncloned, adaptor-ligated *Brassica napus* cv Topas genomic DNA fragments were constructed and used to isolate BNM3 genomic sequences by nested PCR. The primary PCR made use of the outer adaptor primer (AP1) supplied by the manufacturer and a BNM3 specific primer with the sequence:

5'-GAGGCAGCGGTCGGATCGTAACAGTACTCT-3' (SEQ ID NO:8). The nested PCR made use of the nested adaptor primer (AP2) supplied by the manufacturer and a BNM3 specific primer with the sequence:

5'-CATAAGGAGAGAGAGAAAAGCCTAACCAGT-3' (SEQ ID NO:9). The primary PCR mixture was then diluted 1:50 and used as template for nested PCR. Both the primary and nested PCRs were performed as recommended by the manufacturer. The nested PCR products were cloned into the pGEMT-Easy vector (Promega) and sequenced. PCR products corresponding to the 5' untranslated genomic regions of both BNM3A and BNM3B cDNAs were identified.

The genomic DNA sequence spanning the BNA3A ATG translational start and TAG translational stop codons was isolated by PCR from *B. napus* cv Topas genomic DNA using Pfu polymerase (Stratagene) and the following primer combination:

5'-ACCAAGAACTCGTTAGATC-3' (SEQ ID NO:10); and 5'-AACGCATATAACTAAAGATC-3' (SEQ ID NO:11).

The primers were used under standard PCR conditions. The PCR products were cloned into the pGEMT-Easy vector and sequenced.

DNA Gel Blot Analysis and Mapping in *Arabidopsis Thaliana*

Five hundred nanograms of *arabidopsis* genomic DNA (ecotypes Columbia and Landsberg erecta) (Shure et al., 1983) was digested with 20 different restriction endonucleases, separated by electrophoresis through 0.8% agarose gels and blotted onto Hybond N$^+$ nylon membrane (Amersham) using standard methods. Blots were hybridised (1.5 M NaCl, 65° C.) with a $^{32}$P[dATP] random primers labelled probe (Megaprime, Amersham) corresponding to either:

1) approximately the first 405 bp of the BNM3A cDNA (SEQ ID NO.1), or
2) approximately the last 1200 nt of the BNM3A cDNA (SEQ ID NO.1) and then washed under conditions of low stringency (2×SSC, 0.1% SDS at 65° C.) or moderate stringency (0.2×SSC, 0.1% SDS at 25° C.).

A restriction fragment length polymorphism (RFLP) was identified between ecotypes Columbia and Landsberg erecta using the Cfo I restriction endonuclease. This RFLP was used to map the position of the *arabidopsis* BNM3 homologue on the *arabidopsis* genome using the Lister and Dean recombinant inbred (RI) lines (Lister and Dean, 1993). DNA from 100 recombinant inbred lines generated from a cross between ecotypes Columbia and Landsberg erecta was digested with Cfo I, transferred to Hybond N$^+$ nylon membrane, hybridised with the BNM3A cDNA (as above) and washed under conditions of low stringency. The resulting RFLP data was sent to the RI database at the Nottingham *Arabidopsis* Stock Centre for determination of the map location (Lander et al., 1987). The results are discussed in Example 2—2, below.

Isolation of *Arabidopsis Thaliana* Genomic DNA Sequences

Three genome equivalents of an amplified *arabidopsis* ecotype C24 genomic Lambda phage library (Lambda-GEM 11, Promega) were screened using a truncated BNM3A cDNA probe (approximately the last 1200 nt of SEQ ID NO.1). Blots were hybridised with the $^{32}$P-[dATP] random primers labelled probe (as above) and then washed under conditions of low stringency (2×SSC, 0.1% SDS at 65° C.). Seven Lambda phage were initially identified. Three putative full-length Lambda phage clones containing the *arabidopsis* homologue of the BNM3 gene (SEQ ID NO:6) were subsequently identified after hybridisation under conditions of low stringency with a probe derived from the 5' end of the *Brassica napus* BNM3 cDNA (nt 1–405 of SEQ ID NO1). Individual clones comprising approximately 8.0 kb of overlapping sequence were identified from each of the three phage, subcloned into pBR322 and sequenced.

Plasmid Construction for Plant Transformation

The construction of a plasmid vectors containing the BNM3 cDNAs under control of either a POLYUBIQUITIN or Cauliflower Mosaic virus 35S promoter are described below. The plasmid pRAP2TUBI contains a modified *Helianthus annus* POLYUBIQUITIN promoter (Binet et al., 1991) in the plasmid pRAP2T. The plasmid pRAP2T consists of the pUCAP plasmid (van Engelen et al., 1995) and a nopaline synthase (nos) terminator inserted into the Sac 1 and Eco R1 restriction sites. A PCR fragment of the POLYUBIQUITIN UbB1 promoter comprising the 5' end of the promoter to 7 bp from the 3' end of the first exon was amplified from the vector using an M13 reverse primer and the UBIQ-3' primer:

5'-CCATGGATCCAGAGACGAAGCGAAAC-3' (SEQ ID NO:12) which includes introduced Nco I and Bam HI restriction sites. The POLYUBIQUITIN promoter fragment was digested with Pst I and Bam HI, gel purified and ligated into the Pst I and Bam HI sites of pRAP2T, creating the vector pRAP2TUBIHa. The full-length BNM3B cDNA was digested with Eco RI and Xho I restriction enzymes, blunted with Klenow enzyme, gel purified and ligated into the Sma I site of pRAP2TUBI making the plasmid pKB1S. An Asc I/Pac I DNA restriction fragment containing the modified POLYUBIQUITIN promoter, the BNM3B cDNA and the nos terminator was gel purified, and ligated to the Asc I/Pac I digested binary vector pBINPLUS (van Engelen et al., 1995), creating the plasmid pKBBIN1S.

The construction of a vector containing the BNM3A cDNA under control of a double enhanced 35S promoter and AMV translational enhancer was as follows. A Hind III/Xba I DNA restriction fragment containing the double 35S promoter and the AMV translational enhancer from plasmid pBI525 (Datla et al., 1993) was ligated to Hind III/Xba I digested pRAP2T, creating the plasmid pRAP2T35S. An Nco I site was introduced into the BNM3A cDNA clone by site directed mutagenesis. The sequence of the BNM3ANCO1 primer used for mutagenesis is:

5'-ACTCCATGGATAATAACTGGTTAGGC-3' (SEQ ID NO:13). A second primer, BNM3AHINDIII:

5'-AAATTCTCAAGCTTTGGTCCATCTFG-3' (SEQ ID NO14) was used together with the BNM3ANCO1 primer to amplify a 305 bp fragment of the BNM3A cDNA. This PCR fragment was digested with Nco I and Hind III and ligated to Nco I/KpnI cut pRAP2T35S and a Hind III/Kpn I fragment containing the region of the BNM3A cDNA downstream of the Hind III site, creating the vector p35S:BNM3. p35S:BNM3 was digested Asc I and Pac I restriction enzymes and the fragment containing the double 35S promoter, the AMV translational enhancer, the BNM3A cDNA and the nos terminator was gel purified and ligated to the Asc I/Pac I digested binary vector pBINPLUS, creating the plasmid p35S:BNM3BIN.

Both the pKBBIN1S and p35S:BNM3BIN plasmids were transferred to *Agrobacterium tumefaciens* C58C1 strain carrying the disarmed Ti plasmid pMP90 and used in transformation experiments.

Plant Transformation

*Arabidopsis thaliana* ecotype C24 was used as the recipient in transformation experiments. Plants were transformed using either the floral dip method described in Clough and Bent (1998) or the root transformation method described in Vergunst et al. (1998).

Transgenic *Brassica napus* c.v. "Topas" plants were produced by *Agrobacterium tumaciens*-mediated transformation of microspore-derived embryos. Microspore-derived embryos were cultured for 5 weeks at a density of approximately 1000 embryos per ml. Overnight cultures of *Agrobacterium* were diluted 100 times in B5 medium containing 9% sucrose. Embryos were co-cultivated with the diluted bacteria for 48 hours at 24° C. in darkness, with slow shaking. The embryos were then transferred to NLN13 medium supplemented with 350 mg/L cefotaxim and 200 mg/L vancomycin for at least two weeks in darkness at 25° C.

Embryos were germinated in weak light at 25° C. for about 2 weeks on solid B5 medium supplemented with 2% sucrose, cefotaxim (200 mg/L) and vancomycin (100 mg/L). Well developed hypocotyls from germinated embryos were isolated and transferred to fresh germination medium supplemented with 100 mg/L kanamycin. After two weeks on this medium, explants were subcultured to a similar medium supplemented with kanamycin (25 mg/L). Green, putative transgenic, secondary embryos become visible after one month of selection.

Microscopy

All plant material was fixed overnight at 4° C. in 0.1 M phosphate buffer pH 7.0 containing 4% paraformaldehyde. Samples were washed in 0.1 M phosphate buffer and then dehydrated in a graded ethanol series to 100% ethanol. Samples for scanning electron microscopy were critical point dried in liquid $CO_2$ (Balzers CPD020), and mounted on SEM stubs using conductive carbon glue. Samples were coated with 30 nm palladium/gold using a Polaron E5100 sputter coater. Samples were observed in a JEOL JSM 5200 scanning electron microscope with an acceleration voltage of 15 kV. Digital images were obtained using Orion Framegrabber. Samples for light microscopy were embedded in Technovit 7100 (Kulzer). Sections were stained for 10 seconds in 1% Toluidine blue in 1% sodiumtetraborate, rinsed with water and mounted in Euparal. Digital images were recorded using a Sony 3 CCD camera.

Regeneration Experiments

Wild-type and transgenic *arabidopsis* seeds were surface sterilized, plated on ½ MS media containing 20% sucrose (½MS-20) and grown at 21° C. with the plates inclined at a 60° angle. Eight wild-type seedlings and eight seedlings from each of seven independent transgenic lines were harvested 10 days after germination and separated into root, hypocotyl and leaf explants. This material was then divided into two batches. Half of the explants were continuously cultured on B5 media containing 20% glucose (B5-20). Explants were transferred to fresh B5-20 media every two weeks. The remaining explants were cultured on B5-20 containing plant growth regulators in order to induce shoot regeneration (Vergunst et al., 1998). These explants were first placed on callus inducing media (CIM; high auxin to cytokinin ratio) for two days and then transferred to shoot inducing media (SIM; high cytokinin to auxin ratio) for the remainder of the culture period. Explants were transferred to fresh SIM media every two weeks.

Example 1

Isolation and Characterization of the BNM3 Genes from *Brassica Napus*

A subtractive screening approach was used to isolate genes preferentially expressed during the induction of *Brassica napus* c.v. Topas microspore embryogenesis (FIG. 1). Two types of microspore cultures were used in the construction of a subtracted probe: embryogenic and non-embryogenic. Embryogenic cultures were obtained by subjecting late uninucleate microspores and early binucleate pollen to a 4 day, 32° C. heat stress treatment. The non-embryogenic sample was obtained by culturing the same starting population of late uninucleate microspores and early binucleate pollen for 1 day at 25° C. followed by 3 days at 32° C. (Pechan et al., 1991). Poly(A) mRNA was isolated from the embryogenic sample and used to synthesize first strand cDNA. The cDNA was then hybridized to an excess of poly(A)$^+$ RNA isolated from a non-embryogenic microspore/pollen sample. The non-hybridizing, single stranded cDNA, enriched for sequences present in the embryogenic sample, but absent or present at a much lower level in the non-embryogenic sample, was recovered, radioactively labelled and used as a subtracted probe for screening a cDNA library derived from the embryogenic sample described above. Plaques hybridizing to the subtracted probe, but not to a probe derived from the non-embryogenic sample, were selected and subjected to two subsequent rounds of differential screening. Seven independent cDNA clones, comprising six unique DNA sequences were found to be differentially expressed between the embryogenic and non-embryogenic samples. One of these clones, 42A1, later renamed BNM3A (for *Brassica napus* microspore embryo), was further characterized.

Example 2-1

The BNM3 Genes Encode New Members of the AP2 Domain Class of Transcriptional Activators A single BNM3 cDNA clone, BNM3A, was isolated after screening an embryogenic microspore cDNA library with a subtracted probe enriched for genes expressed in embryogenic microspores and pollen. The discrepancy between the size of the cDNA clone (1.2 kb) and the size of the transcript detected on RNA gel blots (2.2 kb) indicated that this clone did not represent a full-length cDNA. Two longer cDNA clones, corresponding to the full length cDNA of the clone originally isolated, BNM3A (SEQ ID NO. 1), and a new clone, BNM3B (SEQ ID NO. 3), were isolated from a 10 day old *Brassica napus* microspore embryo cDNA library. The alignment of the DNA sequence of these clones is shown in FIG. 2. The two BNM3 cDNA clones are 2011 and 1992 nt in length, and are 97% similar at the nucleotide level, differing only slightly in the length and sequence of their 5' and 3' untranslated regions. Both cDNAs potentially encode 579 amino acid polypeptides (predicted molecular mass of 63.9 kDa, pI of 5.7) that are 97% similar at the amino acid level (FIG. 3).

Figure 4:
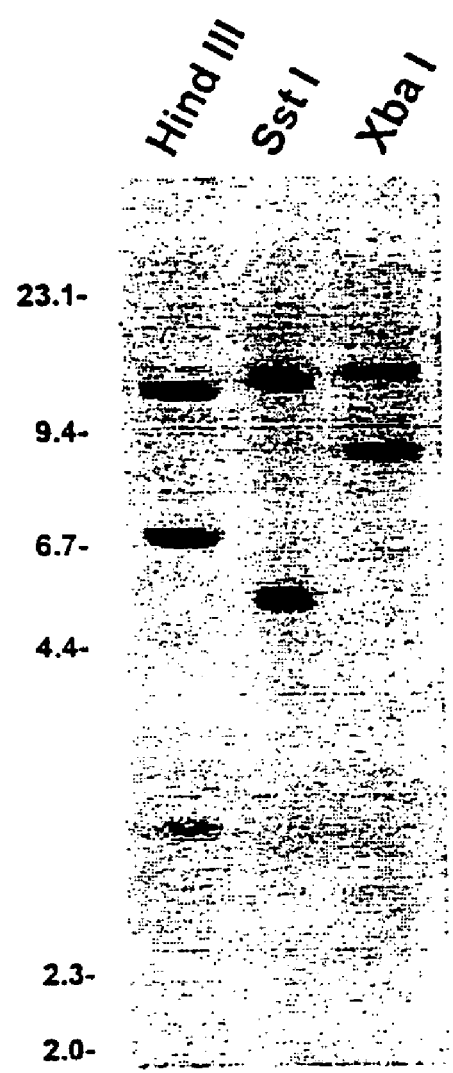
FIG. 4 shows the presence of two BNM3 genes in the Brassica napus genome. A DNA gel blot containing restriction digests of B. napus c.v. Topas genomic DNA was hybridized to a BNM3A cDNA fragment under high stringency conditions. The BNM3A cDNA hybridizes to two DNA fragments under these conditions. These fragments correspond to the BNM3A and BNM3B genes. The position of the molecular size markers (Lambda DNA Hind III restriction fragments) is indicated to the left the figure. The restriction enzymes used to digest the DNA are indicated above the blot.

The genomic complexity of the BNM3 genes was determined by hybridization of the BNM3 cDNAs to gel blots containing *B. napus* genomic DNA (FIG. 4). The BNM3 cDNAs hybridize to two DNA fragments under high stringency conditions. The two hybridizing fragments represent the two BNM3 genes, BNM3A and BNM3B. *B. napus* is an amphidiploid species derived from the hybridization of the diploid *B. rapa* and *B. oleracea* genomes, thus the two BNM3 sequences are likely derived from a single copy locus in each of the parental diploid progenitors.

Search of the sequence databases indicated that the BNM3 translation products contain two copies of an AP2 domain (FIG. 3). The AP2 domain was first identified in APETALA2 (AP2), an *arabidopsis* protein that regulates meristem identity, floral organ specification, seedcoat development and floral homeotic gene expression (Jofuku et al., 1994; WO 98/07842), and has since been identified in a wide range of proteins with diverse functions. These functions range from the activation of genes involved in stress (Zhou, 1997; Stockinger, 1997) and ethylene response (Ohme-Takagi, 1995) to the regulation of leaf, floral and ovule development (Moose, 1996; Jofuku, 1994; Elliot, 1996; Klucher, 1996). The AP2 domain is a 56–68 amino acid repeated motif containing at least two conserved regions: a highly basic YRG element, containing a conserved YRG amino acid motif and the RAYD element. The RAYD element contains a conserved central core of 18 amino acids that is predicted to form an amphipathic a-helix, a structure that is thought to mediate protein—protein interactions. The ability of a number of AP2 domain containing proteins to bind DNA, coupled with the presence of putative nuclear localization signals and acidic regions that may function as transcriptional activators suggests these proteins function as transcription factors.

Two phylogenetically distinct classes of AP2 domain proteins, consisting of either one AP2 domain (EREBP-like) or two AP2 domains connected by a linker region (AP2-like), have been identified (Zhou, 1997). BNM3 belongs to the latter class. Search of the databases with the region corresponding to the two AP2 domains and linker region of BNM3 reveals that BNM3 is most similar to the *arabidopsis* AINTEGUMENTA (ANT; Elliot, 1996;Klucher, 1996) and the *Zea mays* ZMMHCF1 AP2 domain containing protein. (ZM; Daniell, 1996) FIG. 5 shows an alignment of the two AP2 domains of BNM3 with those of other proteins that contain two AP2 domains. BNM3 shares 85% amino acid sequence similarity with ANT and 88% with ZMMHCF1 in this region, but only 66% amino acid similarity with AP2 and GLOSSY15 in this region. A 10 amino acid insertion in the first AP2 domain of the and BNM3 proteins further distinguishes these three proteins from other AP2 domain containing proteins (Elliot, 1996). The BNM3, AINTEGUMENTA and ZMMHCF1 proteins also share a small hydrophobic amino acid motif, LG/SFSLS, in their amino terminal regions, but otherwise show no significant similarity in their DNA or amino acid sequences outside of the AP2 domains and linker. These results indicate that the BNM3 sequences encode unique members of the AP2 domain family of proteins.

A pairwise alignment of BNM3B cDNA and amino acid, sequences with ANT or ZMMHCF-1 sequences indicated that for the BNM3B nucleotide sequence:

there is a 56% identity with ANT cDNA (over the 1905 nucleotides of ANT) and a 58% identity with ZMM-HCF1 cDNA (over the 1773 nucleotide sequence of ZM);

and for the BNM3B amino acid sequence:

there is a 41% identity of the BNM3B protein with ANT protein (over the 555 amino acid sequence of ANT), and a 46% identity with ZMMHCF1 protein (over 485 amino acid sequence of ZM).

Example 2—2

The *Brassica Napus* BNM3 Genes are Represented by a Single *Arabidopsis Thaliana* Orthologue DNA gel blot analysis of *arabidopsis* genomic DNA hybridised to a number of *Brassica napus* BNM3A cDNA (SEQ ID NO:1) probes under conditions of low and moderate stringency indicated the presence of a single homologue of the *Brassica napus* BNM3 genes in the *arabidopsis* genome. An RFLP was also identified between ecotypes Columbia and Landsberg erecta using the Cfo I restriction endonuclease. This RFLP was used to map the position of the single BNM3 homologue on the *arabidopsis* genome to approximately 34 cM on chromosome 5 (Lister and Dean 1993).

Screening of three genomic equivalents of an *arabidopsis* genomic library identified three Lambda clones containing the putative full length *arabidopsis* BNM3 homologue (At-BBM). Sequence analysis of the three AtBBM clones indicated that they are identical (SEQ ID NO:6). FIGS. 9A and B show respectively the restriction fragment pattern of the isolated *arabidopsis* genomic clones and the pattern of restriction fragments obtained after hybridisation of *arabidopsis* genomic DNA with the *Brassica* BNM3A cDNA probe. Comparison of the two figures indicates that the *arabidopsis* AtBBM genomic clones and the homologue identified through DNA gel blot analysis using a heterologous probe are the same. Sequence analysis of the AtBBM genomic clones also positioned the 5' end of the IRREGULAR XYLEM3 (IXR3) gene downstream of the putative AtBBM coding region (position 7479, FIG. 9A). IXR3 has previously been shown to map to a 150 kb region of chromosome 5 between the markers nga106 (33.26 cM) and mi438 (33.34 cM; Taylor et al., 1999). Together this data indicates that the *arabidopsis* orthologue of the *Brassica* BNM3 genes is encoded by a single gene that maps to chromosome 5. A sequence that is very similar with AtBBM, TAMU BAC clone:T10B6 (accession number AP002073; Nakamura, May 18, 2000) also maps to chromosome 5.

Comparison of the structure of *Brassica* BNM3A genomic clone (SEQ ID NO:5) and the *arabidopsis* AtBBM genomic clone (SEQ ID NO:6) indicate that the predicted intron/exon boundaries are highly conserved between the two sequences. Both sequences are predicted to comprise nine exon and eight intron sequences.

Comparison of the DNA sequence of the AtBBM gene (SEQ ID NO:6) and the two *Brassica* cDNA sequences (SEQ ID NO:1 and SEQ ID NO:3) indicated that the three sequences are 85% similar across the entire putative protein coding region and 95% similar in the 546 nt region spanning the two AP2 domains and the linker region lying between the two AP2 domains. The nucleotide similarity to other related AP2 domain encoding genes such as ANT and the sequence located on clone MOE17 on chromosome 3 (accession number AB025629) in the region spanning the two AP2 domains and the linker region lying between the two AP2 domains is 76% and 78% respectively. Neither ANT nor the sequence on chromosome 3 shows significant DNA similarity to AtBBM outside of the AP2 domain encoding region.

The similarity between the predicted amino acid coding sequence of AtBBM and the two *Brassica* cDNA sequences (SEQ ID NO:1 and SEQ ID NO:3) is approximately 80% across the entire protein coding sequence and approximately 99% in the 182 amino acid region spanning the two AP2 domains and the linker region lying between the two AP2 domains. The amino acid similarity to both ANT and the AP2 domain sequence located on clone MOE17 on chromosome 3 in the amino acid region spanning the two AP2 domains and the linker region lying between the two AP2 domains is approximately 85%. Neither of these two protein sequences shows significant similarity to AtBBM outside of the AP2 domain region of the protein.

Example 3

The BNM3 Genes are Preferentially Expressed in Developing Embryos

RNA gel blot analysis (FIG. 6) was used to determine the pattern of BNM3 gene expression during microspore-derived embryo development, seed development, and in non-seed tissues. Both analyses indicate that the BNM3 genes are preferentially expressed in developing embryos.

RNA gel blot analysis indicates that BNM3 mRNAs are detected in microspore cultures induced to undergo embryogenesis, as well as in the subsequent globular, heart, torpedo and cotyledon stages of microspore-derived embryo development (FIG. 6A). BNM3 mRNAs are not detected in non-embryogenic microspore cultures, in freshly isolated microspores and pollen, or in microspores and pollen continuing gametophytic development in culture (FIG. 6A). RNA gel blot analysis of developing seeds shows that BNM3 expression is first detected 14 days after pollination (14 DAP), corresponding to the heart stage of embryo development. BNM3 expression increases during the early (21 DAP) and mid-cotyledon (28 DAP) stages of embryo development and remains constant thereafter (FIG. 6B). BNM3 transcripts were not detected in any of the non-seed tissues tested, reflecting the low level or absence of transcripts in these tissues.

Example 4

Expression of BNM3 in Vegetative Tissues Promotes Asexual Embryo Formation

In order to determine the function the *Brassica napus* BNM3 proteins, the BNM3 cDNAs were placed under the control of two separate constitutive promoter constructs, a modified sunflower POLYUBIQUITIN promoter construct (hereafter referred to as UBI:BNM3) and a double enhanced 35S promoter construct containing an AMV translational enhancer (hereafter referred to as 35S:BNM3), and introduced into *arabidopsis*. Analysis of the phenotype of the transformants indicates that ectopic over expression of the BNM3 cDNAs promotes the formation of somatic embryos on vegetative structures such as cotyledons, petioles, leaf blades and the shoot apical meristem (FIG. 7). The frequency of transformants producing ectopic embryos, as well as the penetrance of the ectopic embryo phenotype, was greater when the BNM3 gene was expressed under control of the stronger double enhanced 35S promoter-AMV translational enhancer, as compared to the POLYUBIQUITIN promoter. Thus a high threshold level of protein product is required to increase the frequency and penetrance of the ectopic embryo phenotype.

BNM3-derived ectopic embryos contain all of the organ systems and tissue layers found in the developing zygotic embryo. BNM3-derived ectopic embryos are bipolar (FIGS. 7D and E) and consist of an axis, comprised of the hypocotyl and radicle regions, shoot and root meristems, and cotyledons (FIG. 7E). In addition, each organ system contains the characteristic radial arrangement of three specialized tissue layers (epidermis, ground parenchyma and provascular tissue) found in zygotic embryos (FIG. 7E). Continued expression of the BNM3 gene within the developing ectopic embryo leads to a reiteration of the embryo-forming process, with the result that new embryos are continuously formed on the surface of pre-existing embryos (FIGS. 7D and E). These results provide conclusive evidence that expression of a single gene, BNM3, is sufficient to initiate a signal transduction cascade leading to the formation of fully differentiated asexually-derived embryos.

Example 5

Expression of BNM3 Increases the Regeneration Capacity of Plant Tissues

We examined the effect of BNM3 gene expression on the ability of *arabidopsis* plants to regenerate shoots in vitro in the presence or absence of added growth regulators. Leaf, root and hypocotyl explants from 10 day old seedlings of wild-type *arabidopsis* and transgenic *arabidopsis* lines expressing BNM3 under control of the POLYUBIQUITIN promoter were placed on media containing growth regulators to induce first callus formation and then shoot organogenesis. Root explants from transgenic lines show at least a 5-fold increase in shoot regeneration in the presence of hormones as compared to wild-type root explants. (FIG. 8A). These shoots also developed faster in the transgenic explants as compared to the wild-type. Wild-type leaf and hypocotyl explants responded by producing callus on the cut end of the petiole (FIG. 8B). In contrast, explants from transgenic lines immediately produced new shoots (FIG. 8B) or roots from the cut end of the petiole. Transgenic explants that initially produced roots eventually also produced shoots.

Transgenic explants were also able to regenerate in absence of added growth regulators. Wild-type leaf and hypocotyl explants placed on medium lacking growth regulators occasionally produced callus or roots at the cut end of the leaf petiole, however shoots did not regenerate from these structures (FIGS. 8C,D). Wild-type roots greened and formed thickened nodule-like structures at the junction with lateral roots, but did not develop further. In contrast, transgenic explants placed on media lacking growth regulators regenerated shoots either from the cut end of the leaf and hypocotyl explants or from the nodule-like structures of root explants (FIGS. 8C,D).

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Anderson, N. L. and Anderson, N. G. (1998). Proteome and proteomics: new technologies, new concepts and new words. Electrophoresis 19, 1853–1861.

Angenent, G. C., Franken, J., Busscher, M., van Dijken, A., van Went, J. L., Dons, H. J. M. and van Tunen, A. J. (1995). A novel class of MADS box genes involved in ovule development in Petunia. Plant Cell 7, 1569–1582.

Aoyama, T. and Chua, N. H. (1997). A glucocorticoid-mediated transcriptional induction system in transgenic plants. Plant J. 2, 397–404.

Baszczynski, C. L., and Fallis, L. (1990). Isolation and nucleotide sequence of a genomic clone encoding a new Brassica napus napin gene. Plant Mol. Biol. 14, 633–635.

Binet, M. N., Lepetit, M., Weil, J. H. and Tessier, L. H. (1991). Analysis of a sunflower polyubiquitin promoter by transient expression. Plant Sci. 79, 87–94.

Boutilier, K. A., Gines, M. J., Demoor, J. M., Huang, B., Baszczynski, C. L., Iyer, V. N. and Miki, B. L. (1994). Expression of the BnmNAP subfamily of napin genes coincides with the induction of Brassica microspore embryogenesis. Plant Mol. Biol. 26, 1711–1723.

Brandstatter, I. and Kieber, J. J. (1998). Two genes with similarity to bacterial response regulators are rapidly and specifically induced by cytokinin in Arabidopsis. Plant Cell 10, 1009–1019.

Caddick, M. X., Greenland, A. J., Jepson, I., Krause, K. P., Qu, N., Riddell, K. V., Salter, M. G., Schuch, W., Sonnewald, U., and Tomsett, A. B. (1998). An ethanol inducible gene switch for plants used to manipulate carbon metabolism. Nature Biotech. 16, 177–180.

Chaudury, A. M., Letham, D. S., Craig, S. and Dennis, E. S. (1993). amp-1-a mutant with higher cytokinin levels and altered embryonic pattern, faster vegetative growth, constitutive photomorphogenesis and precocious flowering. Plant J. 4, 907–916.

Chaudhury, A., Ming, L., Miller, C., Craig, S., Dennis, E. S., and Peacock, W. J. (1997). Fertilization-independent deed development in Arabidopsis thaliana. Proc. Natl. Acad. Sci. USA 94, 4223–4228.

Clough, S. J. and Bent, A. F. (1998). Floral dip: a simplified method for Agrobacterium-mediated transformation of Arabidopsis thaliana. Plant J. 16, 735–743.

Custers, J. B. M, Oldenhof, M. T., Schrauwen, J. A. M., Cordewener, J. H. G., Wullems, G. J. and van Lookeren Campagne, M. M. (1997) Analysis of microspore-specific promoters in tobacco. Plant Mol. Biol. 35, 689–699.

Crouch, M. L., Tenbarge, K. M., Simon, A. E. and Ferl, R. (1983). cDNA clones for Brassica napus seed storage proteins: evidence from nucleotide sequence analysis that both subunits of napin are cleaved from a precursor polypeptide. J. Mol. Appl. Genet. 2, 273–283.

Daley, M., Knauf, V. C., Summerfelt, K. R. and Turner, J. C. (1998). Co-transformation with one Agrobacterium tumefaciens strain containing two binary plasmids as a method for producing marker free transgenic plants. Plant Cell Rep. 17, 489–496.

Daniell, T. J., Fordham-Skelton, A. P., Vergani, P. and Edwards, R. (1996). Isolation of a maize cDNA (accession no. Z47554) (PGR 96-013) encoding APETALA-2-like binding domains by complementation cloning of an L-isoaspartyl methyltransferase-deficient mutant of Escherichia coli. Plant Phys. 110, 1435.

Datla, R. S. S., Bekkaoui, F., Hammerlindl, J. K., Pilate, G., Dunstan, D. I. and Crosby, W. L. (1993). Improved high-level constitutive foreign gene expression in plants using an AMV RNA4 untranslated leader sequence. Plant Sci. 94, 139–149.

DeBlock, M. DeBrower, D. and Tenning, P. (1989). Transformation of Brassica napus and Brasica oleracea using Agrobacterium tumefaciens and the expression of the bar and neo genes in the transgenic plants. Plant Physiol. 91: 694–701.

Dellaert, L. M. W. (1981) Comparison of X-ray and fast neutron-induced mutant spectra. Experiments in Arabidopsis thaliana (L.) Heynh. Arabidopsis Inf. Ser., 18, 16–36.

Doan, D. N. P., Linnestad, C., and Olsen, O.-A. (1996). Isolation of molecular markers from the barley endosperm coenocyte and the surrounding nucellus cell layers. Plant Mol. Biol. 31: 877–886.

Elliot, R. C., Betzner, A. S., Huttner, E., Oakes, M. P., Tucker, W. Q. J., Gerentes, D., Perez, P. and Smyth, D. R. (1996). AINTEGUMENTA, an APETALA2-like gene of arabidopsis with pleiotropic roles in ovule development and floral organ growth. Plant Cell 8, 155–168.

Federoff, N., Furtek, D., and Nelson O. (1984). Cloning of the bronze locus in maize by a simple and general procedure using the transposable controlling element Ac. Proc. Natl. Acad. Sci. USA 81, 3825–3829.

Feldman, K. A., Marks, M. D., Christianson, M. L., and Quatrano, R. S. (1989). A dwarf mutant Arabidopsis generated by T-DNA insertion mutagenesis. Science 243, 1351–1354.

Fobert, P. R., Miki, B. L., and Iyer, V. N. (1991). Detection of gene regulatory signals in plants revealed by T-DNA-mediated fusions. Plant Mol. Biol. 17, 837–851.

Gatz, C. (1997). Chemical control of gene expression. Ann. Rev. Plant Physiol. Plant Mol. Biol. 48, 89–108.

Gatz, C. and Lenk, I. R. P. (1998). Promoters that respond to chemical inducers. Trends Plant Sci. 3, 352–358.

Guerche, P., Tire, C., Grossi De Sa, F., De Clercq, A., Van Montagu, M. and Krebbers, E. (1990). Differential expression of the Arabidopsis 2S albumin genes and the effect of increasing gene family size. Plant Cell 2, 469–478.

Gustavsson, H. O., Ellerstrom, M., Stulberg, K., Ezcurra, I., Koman, A., Hoglund, A., Rask, L. and Josefsson, L.-G. (1991). Distinct sequence elements in a napin promoter interact in vitro with DNA-binding proteins from Brassica napus. Physiol. Plant 82, 205–212.

Haseloff, J. and Amos, B. (1995). GFP in plants. Trends Genet. 11, 328–329.

Jefferson, R. A. and Bicknell, R. (1996). The potential impacts of apomixis:a molecular genetics approach. In The Impact of Plant Molecular Genetics, B. W. S. Sobral, ed (Boston: Birkhanser), pp. 87–101.

Jefferson, R. A., Kavanagh, T. A. and Bevan, M. W. (1987). GUS fusions: β-glucuronidase as a sensitive and versalite gene fusion marker in higher plants. EMBO J. 6, 3901–3907.

Jofuku, K. D., den Boer, B. G. W., van Montagu, M. and Okamuro, J. K. (1994). Control of *Arabidopsis* flower and seed development by the homeotic gene APETALA2. Plant Cell 6, 1211–1225.

Kakimoto, T. (1996). CK17, a histidine kinase homolog implicated in cytokinin signal transduction. Science 274, 982–985.

Keller, W. A., Fan, Z., Pechan, P., Long, N., Grainger, J. (1987). An efficient method for culture of isolated microspores of *Brassica napus*. Proceedings of the 7th International Rapeseed Congress. Poznan, Poland. Vol. 1, 152–157.

Klein, T. M., Wolf, E. D., Wu, R. and Sanford, J. C. (1987). High-velocity microprojectiles for delivering nucleic acids into living cells. Nature 327,70–73

Klimyuk, V. I. and Jones, J. D. G. (1997). AtDMC1, the *Arabidopsis* homologue of the yeast DMC1 gene: characterization, transposon-induced allelic variation and meiosis-associated expression. Plant J. 11, 1–14.

Klucher, K. M., Chow, H., Reiser, L. and Fischer, R. L. (1996). The AINTEGUMENTA gene of *Arabidopsis* required for ovule and female gametophyte development is related to the floral homeotic gene APETALA2. Plant Cell 8, 137–153.

Koltunow, A. M., Bicknell, R. A. and Chaudhury, A. M. (1995). Apomixis: molecular strategies for the generation of genetically identical seeds without fertilization. Plant Physiol. 108,1345–1352.

Koltunow, A. M. (1993). Apomixis: embryo sacs and embryos formed without meiosis or fertilization in ovules. Plant Cell 5, 1425–1437.

Korneef, M., Hanhart, C. J. and Thiel, F. (1989). A genetic and phenotypic description of eceriferun (cer) mutants in *Arabidopsis thaliana*. J. Hered. 80, 118–122.

Lander, E. S., Green, P., Abrahamson, J., Barlow, A., Day, M. J., Lincoln, S. E., and Newber, L. (1987). Mapmaker: an interactive computer package for constructing primary genetic linkage maps of experimental and natural populations. Genetics 121, 174–181.

Lightner J., and Caspar, T. (1988) Seed Mutagenesis of *Arabidopsis*. In *Arabidopsis* Protocols, J. M. Martinez-Zapater and J. Salinas eds (Totowa, USA: Humana Press).

Lipshultz, R. J., Fodor, S. P. A., Gingeras, T. R. and Lockhart, D. J. (1999). High density synthetic oligonucleotide arrays. Nature Genetics 21, 20–24.

Lister, C., and Dean, C. (1993). Recombinant inbred lines for mapping RFLP and phenotypic markers in *Arabidopsis thaliana*. Plant Journal 4, 745–750.

Lotan, T., Ohto, M., Matsudaira Yee, K., West, M. A. L., Lo, R., Kwong, R. W., Yamagishi, K., Fischer, R. L., Goldberg, R. B. and Harada, J. J. (1998). *Arabidopsis* LEAFY COTYLEDON1 is sufficient to induce embryo development in vegetative cells. Cell 93, 1195–1205.

Meijer, A. H., Ouwerkerk, P. B. F. and Hoge, J. H. C. (1998). Vectors for transcription factor cloning and target site identification by means of genetic selection in yeast. Yeast 14, 1407–1415.

Moose, S. P. and Sisco, P. H. (1996). Glossy15, an APETALA2-like gene from maize that regulates leaf epidermal cell identity. Genes Dev. 10, 3018–3027.

Mordhorst, A. P., Toonen, M. A. J. and de Vries, S. C. (1997). Plant embryogenesis. Crit. Rev. Plant Sci. 16, 535–576.

Mordhorst, A. P., Voerman, K. J., Hartog, M. V., Meijer, E. A., van Went, J., Koomneef, M., and de Vries, S. C. (1998). Somatic embryogenesis in *Arabidopsis thaliana* is facilitated by mutations in genes repressing meristematic cell divisions. Genetics 149, 549–563.

Ogas, J., Cheng, J.-C., Sung, R. Z. and Somerville, C. (1997). Cellular differentiation regulated by gibberellin in the *Arabidopsis thaliana* pickle mutant. Science 277, 91–94.

Ohme-Takagi, M. and Shinshi, H. (1995). Ethylene-inducible DNA binding proteins that interact with an ethylene responsive element. Plant Cell 7, 173–182.

Oldenhof, M. T., de Groot, P. F. M., Visser, J. H., Schrauwen, J. A. M. and Wullems, G. J. (1996). Isolation and characterization of a microspore-specific gene from tobacco. Plant Mol. Biol. 31, 213–225.

Ouellet, T., Rutledge, R. G. and Miki, B. L. (1992). Members of the acetohydroxyacid synthase multigene family of *Brassica napus* have divergent patterns of expression. Plant J. 2, 321–330.

Ow, D. W., Jacobs, J. D. and Howell, S. H. (1987). Functional regions of the cauliflower mosaic virus 35S RNA promoter determined by use of the firefly luciferase gene as a reporter for promoter activity. Proc. Natl. Acad. Sci. USA 84, 4870–4874.

Ozias-Akins, P., Lubbers, E. L., Hanna, W. W. and McNay, J. W. (1993). Transmission of the apomictic mode of reproduction in *Pennisetum*: co-inheritance of the trait and molecular markers. Theor. Appl. Genet. 85, 632–638.

Pang, P., Pruitt, R. and Meyerowitz, E. (1988). Molecular cloning, genomic organisation, expression and evolution of the 12S storage protein genes of *Arabidopsis thaliana*. Plant Mol. Biol. 11, 805–820.

Peacock, W. J., Ming, L., Craig, S., Dennis, E., Chaudury, A. M. (1995). A mutagenesis programme for apomixis genes in *Arabidopsis*. In Proceedings Symposium on Induced Mutations and Molecular Techniques for Crop Improvement, (Vienna: International Atomic Energy Agency), pp, 117–125

Pechan, P. M., Bartels, D., Brown, D. C. W. and Schell, J. (1991). Messenger-RNA and protein changes associated with induction of *Brassica* microspore embryogenesis. Planta 184, 161–165.

Roberts, M. R., Foster, G. D., Blundell, R. P., Robinson, S. W., Kumar, A., Draper, J. and Scott, R. (1993). Gametophytic and sporophytic expression of an anther-specific *Arabidopsis thaliana* gene. Plant J. 3, 111–120.

Rounsley, S. D., Ditta, G. S. and Yanofsky, M. F. (1995). Diverse roles for MADS box genes in *Arabidopsis* development. Plant Cell 7, 1259–1269.

Salter, M. G., Paine, J. A., Riddell, K. V., Jepson, I., Greenland, A. J., Caddick, M. X., Tomsett, A. B. (1998). Characterisation of the ethanol-inducible alc gene expression system for transgenic plants. Plant Journal 16, 127–132.

Sambrook, J., Fritsch, E. F. and Maniatis, T. (1989). Molecular Cloning: A Laboratory Manual, second edition. (Cold Spring Harbor: Cold Spring Harbor Laboratory Press).

Schmidt, E. D. L., Guzzo, F., Toonen, M. A. J. and de Vries, S. C. (1997). A leucine-rich repeat containing receptorlike kinase marks somatic plant cells competent to form embryos. Development. 124, 2049–2062.

Shure, M., Wessler, S., and Fedoroff, N. Molecular identification and isolation of the Waxy locus in maize. Cell. 1983 November; 35, 225–33.

Stockinger, E. J., Gilmour, S. J. and Thomashow, M. F. (1997). *Arabidopsis thaliana* CBF1encodes an AP2 domain-containing transcriptional activator that binds to the C-repeat/DRE, a cis-acting DNA regulatory element that stimulates transcription in response to low temperature and water deficit. Proc. Natl. Acad. Sci. USA 94, 1035–1040.

Taylor, R. L. (1967). The foliar embryos of Malaxis paludosa. Can. J. Bot. 45, 1553–1556.

Taylor, N. G., Scheible, W. R., Cutler, S., Somerville, C. R., and Turner, S. R. (1999). The irregular xylem3 locus of *arabidopsis* encodes a cellulose synthase required for secondary cell wall synthesis. Plant cell 11, 769–779.

Treacy, B. K., Hattori, J., Prud' homme, I., Barbour, E., Boutilier, K., Baszczynski, C. L., Huang, B., Johnson, D. A. and Miki, B. L. (1997). Bnm1, a *Brassica* pollen-specific gene. Plant Mol. Biol. 34, 603–611.

Twell, D., Wing, R., Yamaguchi, J. and McCormick, S. (1989). Isolation and expression of an anther-specific gene from tomato. Mol. Gen. Genet. 217, 240–245.

Ulmasov, T., Murfett, J., Hagen, G. and Guilfoyle, T. (1997). Aux/IAA proteins repress expression of reporter genes containing natural and highly active synthetic auxin response elements. Plant Cell 9, 1963–1971.

van Engelen, F. A., Molthoff, J. W., Conner, A. J., Nap, J. P., Pereira, A. and Stiekema, W. J. (1995). pBINPLUS: an improved plant transformation vector based on pBIN19. Transgenic Res. 4, 288–290.

Vergunst, A. C., de Waal, E. C. and Hooykaas, P. J. J. (1998). Root transformation by *Agrobacterium tumefaciens*. In *Arabidopsis* Protocols, J. M. Martinez-Zapater and J. Salinas, eds (Totowa, USA: Humana Press).

Xu, D., McElroy, D., Thornburg, R. W. and Wu, R. C. S. (1993). Systemic induction of a potato pin2 promoter by wounding, methyl jasmonate, and abscisic acid in transgenic rice plants. Plant Mol. Biol. 22, 573–588.

Xu, H., Knox, R. B., Taylor, P. E. and Singh, M. B. (1995). Bcp1, a gene required for male fertility in *Arabidopsis*. Proc. Natl. Acad. Sci. USA 92, 2106–2110.

Yarbrough, J. A. (1932). Anatomical and developmental studies of the foliar embryos of *Bryophyllum calicyinum*. Amer. J. Bot. 19, 443–453.

Yeung, E. C. (1995). Structural and developmental patterns in somatic embryogenesis. In In Vitro Embryogenesis in Plants, T. A. Thorpe, ed (Dordrecht: Kluwer Academic Publishers), pp. 205–247.

Zarsky, V., Garrido, D., Eller, N., Tupy, J., Vicente, O., Sch ffl, F. and Heberle-Bors, E. (1995). The expression of a small heat shock gene is activated during induction of tobacco pollen embryogenesis by starvation. Plant Cell Environ. 18, 139–147.

Zhou, J., Tang, X. and Martin, G. B. (1997). The Pto kinase conferring resistance to tomato bacterial speck disease interacts with proteins that bind a cis-element of pathogenesis-related genes. EMBO J. 16, 3207–3218.

The invention claimed is:

1. An isolated DNA molecule encoding SEQ ID NO:2.
2. An isolated DNA molecule encoding SEQ ID NO:4.
3. An isolated DNA molecule having the nucleotide sequence of SEQ ID NO: 1.
4. An isolated DNA molecule having the nucleotide sequence of SEQ ID NO: 3.

* * * * *

SEQUENCE LISTING

```
<160> NUMBER OF SEQ ID NOS: 17

<210> SEQ ID NO 1
<211> LENGTH: 2014
<212> TYPE: DNA
<213> ORGANISM: Brassica napus

<400> SEQUENCE: 1
gttcatctct cttctttaag accaaaacct ttttctcctc ctcttcatgc atgaaccta      60 actaagttct tcttctttta ccttttacca agaactcgtt agatcactct ctgaactcaa   120
tgaataataa ctggttaggc ttttctctct ctccttatga acaaaatcac catcgtaagg   180
acgtctactc ttccaccacc acaaccgtcg tagatgtcgc cggagagtac tgttacgatc   240
cgaccgctgc ctccgatgag tcttcagcca tccaaacatc gtttccttct ccctttggtg   300
tcgtcgtcga tgctttcacc agagacaaca atagtcactc ccgagattgg gacatcaatg   360
gttgtgcatg caataacatc cacaacgatg agcaagatgg accaaagctt gagaatttcc   420
ttggccgcac caccacgatt tacaacacca acgaaaacgt tggagatgga agtggaagtg   480
gctgttatgg aggaggagac ggtggtggtg gctcactagg actttcgatg ataaagacat   540
ggctgagaaa tcaacccgtg gataatgttg ataatcaaga aaatggcaat gctgcaaaag   600
gcctgtccct ctcaatgaac tcatctactt cttgtgataa caacaacgac agcaataaca   660
acgttgttgc ccaagggaag actattgatg atagcgttga agctacaccg aagaaaacta   720
ttgagagttt tggacagagg acgtctatat accgcggtgt tacaaggcat cggtggacag   780
gaagatatga ggcacattta tgggataata gttgtaaaag agaaggccaa acgcgcaaag   840
```

```
gaagacaagt ttatttggga ggttatgaca agaagaaaa agcagctagg gcttatgatt      900
tagccgcact caagtattgg ggaaccacca ctactactaa cttccccatg agcgaatatg      960
aaaaagaggt agaagagatg aagcacatga caaggcaaga gtatgttgcc tcactgcgca     1020
ggaaaagtag tggtttctct cgtggtgcat cgatttatcg tggagtaaca agacatcacc     1080
aacatggaag atggcaagct aggataggaa gagtcgccgg taacaaagac ctctacttgg     1140
gaacttttgg cacacaagaa gaagctgcag aggcatacga cattgcggcc atcaaattca     1200
gaggattaac cgcagtgact aacttcgaca tgaacagata caacgttaaa gcaatcctcg     1260
aaagccctag tcttcctatt ggtagcgccg caaaacgtct caaggaggct aaccgtccgg     1320
ttccaagtat gatgatgatc agtaataacg tttcagagag tgagaatagt gctagcggtt     1380
ggcaaaacgc tgcggttcag catcatcagg gagtagattt gagcttattg caccaacatc     1440
aagagaggta caatggttat tattacaatg gaggaaactt gtcttcggag agtgctaggg     1500
cttgtttcaa acaagaggat gatcaacacc atttcttgag caacacgcag agcctcatga     1560
ctaatatcga tcatcaaagt tctgtttcgg atgattcggt tactgtttgt ggaaatgttg     1620
ttggttatgg tggttatcaa ggatttgcag ccccggttaa ctgcgatgcc tacgctgcta     1680
gtgagtttga ttataacgca agaaaccatt attactttgc tcagcagcag cagacccagc     1740
agtcgccagg tggagatttt cccgcggcaa tgacgaataa tgttggctct aatatgtatt     1800
accatgggga aggtggtgga gaagttgctc caacatttac agtttggaac gacaattaga     1860
aaaaatagtt aaagatcttt agttatatgc gttgttgtgt gctggtgaac agtgtgatac     1920
tttgattatg ttttttttctt tctcttttttc ttttcttgg ttaatttctt aagacttatt     1980 tttagttttcc attagttgga taaattttca gact                                 2014
```

<210> SEQ ID NO 2
<211> LENGTH: 579
<212> TYPE: PRT
<213> ORGANISM: Brassica napus

<400> SEQUENCE: 2

```
Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160
```

-continued

```
Gly Leu Ser Leu Ser Met Asn Ser Ser Thr Ser Cys Asp Asn Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Thr Thr Thr
                260                 265                 270

Thr Asn Phe Pro Met Ser Glu Tyr Glu Lys Val Glu Glu Met Lys
                275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
                340                 345                 350

Tyr Asp Ile Ala Ala Ile Lys Phe Arg Gly Leu Thr Ala Val Thr Asn
                355                 360                 365

Phe Asp Met Asn Arg Tyr Asn Val Lys Ala Ile Leu Glu Ser Pro Ser
370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His His Gln Gly Val
                420                 425                 430

Asp Leu Ser Leu Leu His Gln His Gln Glu Arg Tyr Asn Gly Tyr Tyr
                435                 440                 445

Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Ser Val Thr Val
                485                 490                 495

Cys Gly Asn Val Val Gly Tyr Gly Tyr Gln Gly Phe Ala Ala Pro
                500                 505                 510

Val Asn Cys Asp Ala Tyr Ala Ala Ser Glu Phe Asp Tyr Asn Ala Arg
                515                 520                 525

Asn His Tyr Tyr Phe Ala Gln Gln Gln Thr Gln Gln Ser Pro Gly
                530                 535                 540

Gly Asp Phe Pro Ala Ala Met Thr Asn Val Gly Ser Asn Met Tyr
545                 550                 555                 560

Tyr His Gly Glu Gly Gly Gly Glu Val Ala Pro Thr Phe Thr Val Trp
                565                 570                 575

Asn Asp Asn
```

<210> SEQ ID NO 3
<211> LENGTH: 2011
<212> TYPE: DNA
<213> ORGANISM: Brassica napus

<400> SEQUENCE: 3

```
ttcttctttt accttttacc aagaactcgt tagatcattt tctgaactcg atgaataata      60
actggttagg cttttctctc tctccttatg aacaaaatca ccatcgtaag gacgtctgct     120
cttccaccac cacaaccgcc gtagatgtcg ccggagagta ctcttacgat ccgaccgctg     180
cctccgatga gtcttcagcc atccaaacat cgtttccttc tccctttggt gtcgtcctcg     240
atgctttcac cagagacaac aatagtcact cccgagattg gacatcaat ggtagtgcat      300
gtaataacat ccacaatgat gagcaagatg gaccaaaact tgagaatttc cttggccgca     360
ccaccacgat ttacaacacc aacgaaaacg ttggagatat cgatggaagt gggtgttatg     420
gaggaggaga cggtggtggt ggctcactag gactttcgat gataaagaca tggctgagaa     480
atcaacccgt ggataatgtt gataatcaag aaaatggcaa tggtgcaaaa ggcctgtccc     540
tctcaatgaa ctcatctact tcttgtgata acaacaacta cagcagtaac aaccttgttg     600
cccaagggaa gactattgat gatagcgttg aagctacacc gaagaaaact attgagagtt     660
ttggacagag gacgtctata taccgcggtg ttacaaggca tcggtggaca ggaagatatg     720
aggcacattt atgggataat agttgtaaac gagaaggcca aacgcgcaaa ggaagacaag     780
tttatttggg aggttatgac aaagaagaaa agcagctag gcttatgat ttagccgcac       840
tcaagtattg gggaaccacc actactacta cttccccat gagcgaatat gagaaagaga      900
tagaagagat gaagcacatg acaaggcaag agtatgttgc ctcacttcgc aggaaaagta     960
gtggtttctc tcgtggtgca tcgatttatc gtggagtaac aagacatcac caacatggaa    1020
gatggcaagc taggatagga agagtcgccg gtaacaaaga cctctacttg ggaacttttg    1080
gcacacaaga agaagctgca gaggcatacg acattgcggc catcaaattc agaggattaa    1140
ccgcagtgac taacttcgac atgaacagat acaacgttaa agcaatcctc gaaagcccta    1200
gtcttcctat tggtagcgcc gcaaaacgtc tcaaggaggc taaccgtccg gttccaagta    1260
tgatgatgat cagtaataac gtttcagaga gtgagaataa tgctagcggt tgcaaaacg     1320
ctgcggttca gcatcatcag ggagtagatt tgagcttatt gcagcaacat caagagaggt    1380
acaatggtta ttattacaat ggaggaaact tgtcttcgga gagtgctagg gcttgtttca    1440
aacaagagga tgatcaacac catttcttga gcaacacgca gagcctcatg actaatatcg    1500
atcatcaaag ttctgtttca gatgattcgg ttactgtttg tggaaatgtt gttggttatg    1560
gtggttatca aggatttgca gccccggtta actgcgatgc ctacgctgct agtgagtttg    1620
actataacgc aagaaaccat tattactttg ctcagcagca gcagacccag cattcgccag    1680
gaggagattt tcccgcggca atgacgaata atgttggctc taatatgtat taccatgggg    1740
aagtggtgg agaagttgct ccaacattta cagtttggaa cgacaattag aaataatagt    1800
taaagatctt tagttatatg cgttgttgtg tggtgttgaa cagtttgata ctttgattat    1860
gtttttttt ctcttttca ttttgttggt tagtttctta agacttattt tttgtttcca      1920
ttagttggat aaattttcgg acttaagggt cacttctgtt ctgacttctg tctaatacag    1980
aaaagttttc ataaaaaaaa aaaaaaaaa a                                     2011
```

<210> SEQ ID NO 4

```
<211> LENGTH: 579
<212> TYPE: PRT
<213> ORGANISM: Brassica napus

<400> SEQUENCE: 4

Met Asn Asn Asn Trp Leu Gly Phe Ser Leu Ser Pro Tyr Glu Gln Asn
1               5                   10                  15

His His Arg Lys Asp Val Cys Ser Ser Thr Thr Thr Ala Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Leu Asp
    50                  55                  60

Ala Phe Thr Arg Asp Asn Asn Ser His Ser Arg Asp Trp Asp Ile Asn
65                  70                  75                  80

Gly Ser Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Ile Asp Gly Ser Gly Cys Tyr Gly Gly Gly Asp Gly
        115                 120                 125

Gly Gly Gly Ser Leu Gly Leu Ser Met Ile Lys Thr Trp Leu Arg Asn
130                 135                 140

Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn Asn
                165                 170                 175

Tyr Ser Ser Asn Asn Leu Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Met Ser Glu Tyr Glu Lys Glu Ile Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
        355                 360                 365

Phe Asp Met Asn Arg Tyr Asn Val Lys Ala Ile Leu Glu Ser Pro Ser
    370                 375                 380

Leu Pro Ile Gly Ser Ala Ala Lys Arg Leu Lys Glu Ala Asn Arg Pro
```

```
                385                 390                 395                 400
            Val Pro Ser Met Met Ile Ser Asn Asn Val Ser Glu Ser Glu Asn
                        405                 410                 415
            Asn Ala Ser Gly Trp Gln Asn Ala Ala Val Gln His His Gln Gly Val
                        420                 425                 430
            Asp Leu Ser Leu Leu Gln Gln His Gln Glu Arg Tyr Asn Gly Tyr Tyr
                        435                 440                 445
            Tyr Asn Gly Gly Asn Leu Ser Ser Glu Ser Ala Arg Ala Cys Phe Lys
                        450                 455                 460
            Gln Glu Asp Asp Gln His His Phe Leu Ser Asn Thr Gln Ser Leu Met
            465                 470                 475                 480
            Thr Asn Ile Asp His Gln Ser Ser Val Ser Asp Asp Ser Val Thr Val
                        485                 490                 495
            Cys Gly Asn Val Val Gly Tyr Gly Tyr Gln Gly Phe Ala Ala Pro
                        500                 505                 510
            Val Asn Cys Asp Ala Tyr Ala Ala Ser Glu Phe Asp Tyr Asn Ala Arg
                        515                 520                 525
            Asn His Tyr Tyr Phe Ala Gln Gln Gln Thr Gln Gln Ser Pro Gly
                        530                 535                 540
            Gly Asp Phe Pro Ala Ala Met Thr Asn Asn Val Gly Ser Asn Met Tyr
            545                 550                 555                 560
            Tyr His Gly Glu Gly Gly Glu Val Ala Pro Thr Phe Thr Val Trp
                        565                 570                 575
            Asn Asp Asn

<210> SEQ ID NO 5
<211> LENGTH: 4873
<212> TYPE: DNA
<213> ORGANISM: Brassica napus

<400> SEQUENCE: 5
atctctccac cgattcgtta cccagtgctt gaaaatatga tgactacgaa tcaattaaat      60
ggagaagctc cactgcttgt gtaggtggaa gctcaagcaa caaccggaaa cctcggcgtt     120
atcgggagtt agcatcgtta tttgccaaaa tttccgccgc agagatgaaa cgattcaaga     180
gaaaccctca ataggttag ccataaaaca gtgaattagt atgatttaag agataagaag      240
agaagatgag ttcaagaaaa gaaatactca catctattta tactgtttac acccgcctt     300
tcagatctaa gcaaagcatt gaagatgaat cgtggaggag agttaatagg atttaacaca     360
aagccattaa ccaaaccgtt gcaggtcggg agacgaaccg caaaagtcac gcctagccgt     420
cgcacgaaga ggagcgatga atttcgtttt ctcgctgcag tcgtattagg gatagacgga     480
gctcattatc gttgggccgg aaacacttct aatctcacag cccatgaaca cactaaagaa     540
cgaaaccgaa aatgtttgaa gtttaatgaa acgtgcggtt tgccttatgg acacatgtca     600
ttacgatatg aaatgattta ctacgtggaa tcataggtgt ctctctaagg agagagcaaa     660
ccctatacttt atataaatag atttgtatca ttctaagagg tgtttaagat ttttgcataa     720
atattaaaaa aaaatacaaa tttttatgta attagttttg gttacataaa ataacattaa     780
ataaaattaa ttcaaccaat aaaaaaatac ggtattttat aattggtcaa aaataaaaat     840
aaaacattaa atttcaccta gaattacgag aatgtcactt attttgaaac aaaatcaaaa     900
tcttttaaaca tcaattaaac tgatacggat ggagtatata tctttacaga gaacatatat     960
atatgttttt cttgtaagcg tccatctctt cttagtcatg tagttcaaat accagctgca    1020
```

```
gtaaaaccat gaatatttga atttgttgta aaatattcga agcgactact gcacgtttgg   1080
aagcaaaacg ccaaacgcaa tcgctcgctc ggtcataggg tcacacatac acatgtgact   1140
agcattatgg gtcttaattc aacagcgagt gattttggga tttattatta gttctcgtgt   1200
tactctcact ttaacacaaa gtcactaacc ttatttacac atgaagagag gtttgaaagg   1260
gcttttgact gattaattat aatgtattaa accaaactag aattaagaga ttaggcattg   1320
aattacatta ccaccaccac ccaccattca aaccgaccaa tacatctcca cagttttcaa   1380
gtaaaacaac ttttttttgt tgttccttcg gaatttaaat aaatattcgt ttatataaat   1440
gcgcatgata tgacgcctcg gaagaaatga acattatat ctttgacttt tcttctccta   1500
gttcatctct cttctttaag accaaaacct ttttctcctc ctcttcatgc atgaacccta   1560
actaagttct tcttctttta ccttttacca agaactcgtt agatcactct ctgaactcaa   1620
tgaataataa ctggttaggc ttttctctct ctccttatga acaaaatcac catcgtaagg   1680
acgtctactc ttccaccacc acaaccgtcg tagatgtcgc cggagagtac tgttacgatc   1740
cgaccgctgc ctccgatgag tcttcagcca tccaaacatc gtttccttct cctttggtg   1800 tcgtcgtcga tgcttcacc agagacaaca atagtcactc ccgaggttat tgttttagaa   1860
ctacttgttt tttttttgatt tgtttatttg tttagtttcc tcttcttcca atgcgtagaa   1920
caaagaccaa tacacacgca cgcatactag ccctattttt tccttgggct tatttatcga   1980
tttcatttat tttgagaata tcaatgtgtg gggtttgatg tttgtttgca tatagtaata   2040
ctaaaacata tgccagttat acatagattt tttttaaaga tatacatgga tatgaaatga   2100
aatttgacat ttcctccttt attcaatatc ataatatgat cacatacatg tgtacctttt   2160
gatttgtata tttgtttctt acagttgaag gagagaataa ccaaataccc atttgtatat   2220
tatagatcgg tgatgaaaag taaatttaac aaattatgat aatataggcc attaatcttt   2280 gattttttt ctttatagat tgggacatca atggttgtgc atgcaataac atccacaacg   2340
atgagcaaga tggaccaaag cttgagaatt tccttggccg caccaccacg atttacaaca   2400
ccaacgaaaa cgttggagat ggaagtggaa gtggctgtta tggaggagga gacggtggtg   2460
gtggctcact aggactttcg atgataaaga catggctgag aaatcaaccc gtggataatg   2520
ttgataatca agaaaatggc aatgctgcaa aaggcctgtc cctctcaatg aactcatcta   2580
cttcttgtga taacaacaac gacagcaata acaacgttgt tgcccaaggg aagactattg   2640
atgatagcgt tgaagctaca ccgaagaaaa ctattgagag ttttggacag aggacgtcta   2700
tataccgcgg tgttacaagg tgcccttcat ttatttaatt aaaatgtgta aaatgtcgct   2760
tgaattgtta tcttcttggt aaagtctggg acattgatct aatggctctg ttgcgagagt   2820
gctaccgaat ggtccttgat atatagtatc aaagagagat attgttatta tgggcttata   2880
tagaataata catatatata tatatataca tggtagctgt tgatgacatg tatgttcgta   2940
ttaaatgata aggcatcggt ggacaggaag atatgaggca catttatggg ataatagttg   3000
taaaagagaa ggccaaacgc gcaaaggaag acaaggtata tatatattca ttgataattt   3060
gatcatattt tcatacacga tttactttca aactaatata ggttttttcga tcattgttca   3120 tgtttttatc aaaatttgca cctggtggtt gtcttctcag tttatttggg taagtaattt   3180
attataaatt ggacgaagct gtgatgggta atctaaatt atataatcaa atttgtttat   3240
tttttgtgta tacattcatt atataatcaa aatagcgata cgatctacat tcaattgttg   3300
tctatatcat gcaggaggtt atgacaaaga agaaaaagca gctagggctt atgatttagc   3360
cgcactcaag tattgggaa ccaccactac tactaacttc cccgtaagtc aatcaatgtt   3420
```

-continued

| | |
|---|---|
| gtacaagatt tcataactta gaaccaattt tattctttt ttataagatg ctattatctt | 3480 |
| attattaatt gccatgttta tatcgttaca tttattacaa taaaagtac ttttggtttg | 3540 |
| atataatatg tagatgagcg aatatgaaaa agaggtagaa gagatgaagc acatgacaag | 3600 |
| gcaagagtat gttgcctcac tgcgcaggta tataatggaa cttctgatat tattgcatat | 3660 |
| ggcatctatt attatacatg tatattagta ttttatatat agaacccatc acgctcacgt | 3720 |
| ttatatttaa aaatatgtcc gtattcacgt cagattatca gcatacacct atatataata | 3780 |
| gacattaaaa tatgcaggaa aagtagtggt ttctctcgtg gtgcatcgat ttatcgtgga | 3840 |
| gtaacaaggt attcatacag agagaacgaa tcctattttg ttacgtacat atatatataa | 3900 |
| aaatataatt ataagatatc acattttata ttatgaatat ttcttctaat gggtccaaaa | 3960 |
| gacatcacca acatggaaga tgcaagcta ggataggaag agtcgccggt aacaaagacc | 4020 |
| tctacttggg aacttttggt acgtttagtc ttctcttact aaacttcaca atcaaatcta | 4080 |
| taacaaaaga tatcaactaa aaactacaac atatatctaa gtaagctgta catatattat | 4140 |
| atatgaaggc acacaagaag aagctgcaga ggcatacgac attgcggcca tcaaattcag | 4200 |
| aggattaacc gcagtgacta acttcgacat gaacagatac aacgttaaag caatcctcga | 4260 |
| aagccctagt cttcctattg gtagcgccgc aaaacgtctc aaggaggcta accgtccggt | 4320 |
| tccaagtatg atgatgatca gtaataacgt ttcagagagt gagaatagtg ctagcggttg | 4380 |
| gcaaaacgct gcggttcagc atcatcaggg agtagatttg agcttattgc accaacatca | 4440 |
| agagaggtac aatggttatt attacaatgg aggaaacttg tcttcggaga gtgctagggc | 4500 |
| ttgtttcaaa caagaggatg atcaacacca tttcttgagc aacacgcaga gcctcatgac | 4560 |
| taatatcgat catcaaagtt ctgtttcgga tgattcggtt actgtttgtg gaaatgttgt | 4620 |
| tggttatggt ggttatcaag gatttgcagc cccggttaac tgcgatgcct acgctgctag | 4680 |
| tgagtttgat tataacgcaa gaaaccatta ttactttgct cagcagcagc agacccagca | 4740 |
| gtcgccaggt ggagattttc ccgcggcaat gacgaataat gttggctcta atatgtatta | 4800 |
| ccatggggaa ggtggtggag aagttgctcc aacatttaca gtttggaacg acaattagaa | 4860 |
| aaaatagtta aag | 4873 |

<210> SEQ ID NO 6
<211> LENGTH: 5151
<212> TYPE: DNA
<213> ORGANISM: Arabidopsis thaliana

<400> SEQUENCE: 6

| | |
|---|---|
| tctcaaactc atccatctga ttttaataac agttttttct tcttttctt ttgttgtttt | 60 |
| ttaccacttt tctttcttt tctcattttc tacttacttc cagatttttc attttcctat | 120 |
| ttttggtcac acgctcttgt cagttgtaga tatcttcatc tacaggtgtt tccttttatt | 180 |
| ttcagatgga atctcaatct acaggtgttt ctcacttcaa taaattacgg ccccaaaaa | 240 |
| atttagtttt tgtatttaca agaaacatag cataatatga tacatatggt tttgaagtac | 300 |
| tgttttttac acaaaacttt gattataaaa cctcagccgt tctttcgtat ttagaattta | 360 |
| aacgcatgca atgaagtcat tcgtgaatga tatataaata gtttgtttat ttgttatata | 420 |
| tcgtcccgcc ccggatcaaa acctaaagta agtgaataaa attttctttt gtagagataa | 480 |
| gaaaatttgt accgcgtatc gaaaatgtaa aacctatttt aatttctaga tctactaatt | 540 |
| gggtttgagg tattgaaata attgggtacc aaaggtttgg ggtactatat ataaaaagca | 600 |

-continued

```
gataagaaca aattgttagg aaaaaataat atgattttgt aggtaccgag gcaattctag      660
aacgtgtgtt ggtggtgtgt tagatattgc aggcataata atggaagaag tgaaattata      720
ttacaattaa ataggaagac gagaatccat tgaatcatat cttaccagtc caaactttt      780 ttaagtatat aaatctttga aagagtataa acccatgcac atgcccactt tcgtctcatt      840
gatccatgtg tatacccctat agtttcctcc ctaattactc taattcccct aaatcattt      900 ttaatttgat acaattagtc ggataagctc aaactacttt actattggtg cttagcatgt      960
acagtacata tctagcatcc gaaccctact agccatccac atcttatgta cataattatg     1020
actgttttaa gtactttttt actttcgttt acaatgtttg tttgaaaatt tgaggcgttt     1080
tttactggtt gaactgtagc cactaagaca ctaagacttc aaaattcaaa taggaaaatc     1140 tatacttta caatatcttt gcatgtcaaa ttattttaa cgtggttata cattttgcct      1200
aagatttaga gtacattcat aataacaaca ataaatatt tctatatata gtaggtttag     1260
tgaagttact atatgagata gttcatcgca ttgatcacgt ctgatgcgaa tcacatatcc     1320
tatatctagt tgaacatatg tttcgtggaa gacaggaacc atctcttaga cccgcacttc     1380
aaaatatcac aaaacacgaa accatgaatc ttttgagttt gttaaaaaat actaaaagtg     1440
acgagttcgc gtttggaaaa aatgccaaac taaatcgctg gctcgtgtca tacgttcaca     1500
catacacatg tctctaagag acacagcatc attggtctta aatcgacaac gagtgagttt     1560
ttggactttt acctattggt cctcgacatg tttacccatt tttgtcattt acatttaaca     1620
ttttatacgc atgaagagag agagacagaa agcagagatt tgaaatggtt tttgactgat     1680
taattaaagt gtcatcaaaa caaattggga ttacgagatt atccagttga aacgacatta     1740 ctaccccctac ccttcaaacc gaccaataca tctccacatt tttcaagtaa atatttttc     1800 tttctgaatt taattgcaaa attctctaaa tgcgcataat atgtcgcctc ggaagaaatg     1860
aacattatat ttttgacttt tcttcttctt cttcctcttc tctcttcatt taacaccaaa     1920 accttttct ttctcctctt catgcatgaa ccctaactaa gttctttttc ctattcttct      1980
tctctcatct atcacaagga gtagttagaa tattatatga actcgatgaa taactggtta     2040
ggcttctctc tctctcctca tgatcaaaat catcaccgta cggatgttga ctcctccacc     2100
accagaaccg ccgtagatgt tgccggaggg tactgttttg atctggccgc tccctccgat     2160
gaatcttctg ccgttcaaac atcttttctt tctcctttcg gtgtcaccct cgaagctttc     2220
accagagaca ataatagtca ctcccgaggt ttgtgttta aaaatattta ttttatcttt     2280 gttttttgtta tttttttcccc ttcttccaat gcatagaaca aagaccaaga ctcacgcacg     2340
tagccctatt tttgttttc attgtttatc gatttcatct cttttgagaa tttccatgag     2400
tggggtttag tgtttgttca catgatcaca tctcatgaat ttaaacttag taaaacatga     2460
aactagacat ttatttgta ccctttttatc cttataaaat gaaaattcca tttcgtatat      2520
tatagatcgg tgatgaatca aacccaacgt tggggatcgc tttgtttttt gtctatagat     2580
tgggacatca atggtggtgc atgcaataca ttaaccaata acgaacaaaa tggaccaaag     2640
cttgagaatt tcctcggccg caccaccacg atttacaata ccaacgagac cgttgtagat     2700
ggaaatggcg attgtggagg aggagacggt ggtggtggcg gctcactagg cctttcgatg     2760
ataaaaacat ggctgagtaa tcattcggtt gctaatgcta atcatcaaga caatggtaac     2820
ggtgcacgag gcttgtccct ctctatgaat tcatctacta gtgatagcaa caactacaac     2880
aacaatgatg atgtcgtcca agagaagact attgttgatg tcgtagaaac tacaccgaag     2940
aaaactattg agagttttgg acaaaggacg tctatatacc gcggtgttac aaggttaatt     3000
```

-continued

```
tcattgatct atgtatattt ttattgtgct taaattgtga ttttcttggt attgtttggg      3060
acattctaat ggttcggttg agagagagtg caacggaatg tctctcaatg tatattaaag      3120
agaaacatta attagtgtac atgggtttat atatacaata atacgtcata tatatggtat      3180
gctcttgatc atagtatata atgtttgaat ttaatgtcag gcatcggtgg acaggtagat      3240
acgaggcaca tttatgggac aatagttgca aaagagaagg ccagactcgc aaaggaagac      3300
aaggtactat atatataaag ctaattttt aattttcatt taccatttat tttcaaacta       3360
atttaggttt tcttttcatg tgtttcatca aaatttgcac ctgatggctc tcttttcagt      3420
ttatctgggt aagttcttga ttttaagcta taaattaata atagatgact attaaatcta      3480
ttctaagcaa aatataattg ttgtgttatc tgatcctaca ggaggttatg acaaagaaga      3540
aaaagcagct agggcttacg atttagccgc actaaagtat tggggaccca ccactactac      3600
taacttcccc gtatgttaat taatcaataa tatatacata aattcctaac ttctaaccaa      3660
ttttagtctg aataatgcca atctcttaaa ctagtattat cttactatta actgtcatgt      3720
ttatattgtt acaataaaaa ttagtaatgt tggttggata taatattcag ttgagtgaat      3780
atgagaaaga ggtagaagag atgaagcaca tgacgaggca agagtatgtt gcctctctgc      3840
gcaggtacag aatgaaactc ttgaatttat tgcattttag aaacccatca cgtatatatt      3900
tattaaaata tatcgtaaca ttgaataaat cattatttgg aaagatataa gaaacatgta      3960
aatatgcagg aaaagtagtg gtttctctcg tggtgcatcg atttatcgag gagtaacaag      4020
gtacgtataa tccatctaga tatggaacga atactagtgt ttcattattt tttttgatgt      4080
atacataata attgtcatac aatactatta atctaatcta attaatattt cctttaaaat      4140
ggttccaaaa ggcatcacca acatggaagg tggcaagcta ggatcggaag agtcgccggt      4200
aacaaagacc tctacttggg aactttcggt acattttcca ataaaatcta tatactataa      4260
gatattaaat atacacaaat atatctaagt gaatcataca aattatgtag gcacacagga      4320
agaggctgct gaggcttatg acattgcagc cattaaattc agaggattaa gcgcagtgac      4380
taacttcgac atgaacagat acaatgttaa agcaatcctc gagagcccga gtctacctat      4440
tggtagttct gcgaaacgtc tcaaggacgt taacaatccg gttccagcta tgatgattag      4500
taataacgtt tcagagagtg caaataatgt tagcggttgg caaaacactg cgtttcagca      4560
tcatcaggga atggatttga gcttattgca gcaacagcag gagaggtacg ttggttatta      4620
caatggagga aacttgtcta ccgagagtac tagggtttgt ttcaaacaag aggaggaaca      4680
acaacacttc ttgagaaact cgccgagtca catgactaat gttgatcatc atagctcgac      4740
ctctgatgat tctgttaccg tttgtggaaa tgttgttagt tatggtggtt atcaaggatt      4800
cgcaatccct gttggaacat cggttaatta cgatcccttt actgctgctg agattgctta      4860
caacgcaaga aatcattatt actatgctca gcatcagcaa caacagcaga ttcagcagtc      4920
gccgggagga gattttccgg tggcgatttc gaataaccat agctctaaca tgtactttca      4980
cggggaaggt ggtggagaag gggctccaac gttttcagtt tggaacgaca cttagaaaaa      5040
taagtaaaag atcttttagt tgtttgcttt gtatgttgcg aacagtttga ttctgttttt      5100
cttttttcctt tttttgggta attttcttat aactttttc atagtttcga t                5151
```

<210> SEQ ID NO 7
<211> LENGTH: 581
<212> TYPE: PRT
<213> ORGANISM: Arabidopsis thaliana -continued

<400> SEQUENCE: 7

```
Met Asn Asn Trp Leu Gly Phe Ser Leu Ser Pro His Asp Gln Asn His
1               5                  10                  15

His Arg Thr Asp Val Asp Ser Ser Thr Thr Arg Thr Ala Val Asp Val
            20                  25                  30

Ala Gly Gly Tyr Cys Phe Asp Leu Ala Ala Pro Ser Asp Glu Ser Ser
        35                  40                  45

Ala Val Gln Thr Ser Phe Leu Ser Pro Phe Gly Val Thr Leu Glu Ala
    50                  55                  60

Phe Thr Arg Asp Asn Asn Ser His Ser Arg Asp Trp Asp Ile Asn Gly
65                  70                  75                  80

Gly Ala Cys Asn Thr Leu Thr Asn Asn Glu Gln Asn Gly Pro Lys Leu
                85                  90                  95

Glu Asn Phe Leu Gly Arg Thr Thr Ile Tyr Asn Thr Asn Glu Thr
            100                 105                 110

Val Val Asp Gly Asn Gly Asp Cys Gly Gly Asp Gly Gly Gly
        115                 120                 125

Gly Ser Leu Gly Leu Ser Met Ile Lys Thr Trp Leu Ser Asn His Ser
    130                 135                 140

Val Ala Asn Ala Asn His Gln Asp Asn Gly Asn Gly Ala Arg Gly Leu
145                 150                 155                 160

Ser Leu Ser Met Asn Ser Ser Thr Ser Asp Ser Asn Asn Tyr Asn Asn
                165                 170                 175

Asn Asp Asp Val Val Gln Glu Lys Thr Ile Val Asp Val Val Glu Thr
            180                 185                 190

Thr Pro Lys Lys Thr Ile Glu Ser Phe Gly Gln Arg Thr Ser Ile Tyr
        195                 200                 205

Arg Gly Val Thr Arg His Arg Trp Thr Gly Arg Tyr Glu Ala His Leu
    210                 215                 220

Trp Asp Asn Ser Cys Lys Arg Glu Gly Gln Thr Arg Lys Gly Arg Gln
225                 230                 235                 240

Val Tyr Leu Gly Gly Tyr Asp Lys Glu Glu Lys Ala Ala Arg Ala Tyr
                245                 250                 255

Asp Leu Ala Ala Leu Lys Tyr Trp Gly Pro Thr Thr Thr Thr Asn Phe
            260                 265                 270

Pro Leu Ser Glu Tyr Glu Lys Glu Val Glu Glu Met Lys His Met Thr
        275                 280                 285

Arg Gln Glu Tyr Val Ala Ser Leu Arg Arg Lys Ser Ser Gly Phe Ser
    290                 295                 300

Arg Gly Ala Ser Ile Tyr Arg Gly Val Thr Arg His His Gln His Gly
305                 310                 315                 320

Arg Trp Gln Ala Arg Ile Gly Arg Val Ala Gly Asn Lys Asp Leu Tyr
                325                 330                 335

Leu Gly Thr Phe Gly Thr Gln Glu Glu Ala Ala Glu Ala Tyr Asp Ile
            340                 345                 350

Ala Ala Ile Lys Phe Arg Gly Leu Ser Ala Val Thr Asn Phe Asp Met
        355                 360                 365

Asn Arg Tyr Asn Val Lys Ala Ile Leu Glu Ser Pro Ser Leu Pro Ile
    370                 375                 380

Gly Ser Ser Ala Lys Arg Leu Lys Asp Val Asn Asn Pro Val Pro Ala
385                 390                 395                 400

Met Met Ile Ser Asn Asn Val Ser Glu Ser Ala Asn Asn Val Ser Gly
                405                 410                 415
```

```
Trp Gln Asn Thr Ala Phe Gln His His Gln Gly Met Asp Leu Ser Leu
            420                 425                 430

Leu Gln Gln Gln Glu Arg Tyr Val Gly Tyr Tyr Asn Gly Gly Asn
        435                 440                 445

Leu Ser Thr Glu Ser Thr Arg Val Cys Phe Lys Gln Glu Glu Gln
        450                 455                 460

Gln His Phe Leu Arg Asn Ser Pro Ser His Met Thr Asn Val Asp His
465                 470                 475                 480

His Ser Ser Thr Ser Asp Asp Ser Val Thr Val Cys Gly Asn Val Val
                485                 490                 495

Ser Tyr Gly Gly Tyr Gln Gly Phe Ala Ile Pro Val Gly Thr Ser Val
            500                 505                 510

Asn Tyr Asp Pro Phe Thr Ala Ala Glu Ile Ala Tyr Asn Ala Arg Asn
            515                 520                 525

His Tyr Tyr Tyr Ala Gln His Gln Gln Gln Gln Ile Gln Gln Ser
        530                 535                 540

Pro Gly Gly Asp Phe Pro Val Ala Ile Ser Asn Asn His Ser Ser Asn
545                 550                 555                 560

Met Tyr Phe His Gly Glu Gly Gly Glu Gly Ala Pro Thr Phe Ser
                565                 570                 575

Val Trp Asn Asp Thr
            580
```

<210> SEQ ID NO 8
<211> LENGTH: 30
<212> TYPE: DNA
<213> ORGANISM: Artificial
<220> FEATURE:
<223> OTHER INFORMATION: Primer

<400> SEQUENCE: 8
gaggcagcgg tcggatcgta acagtactct                                30

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
cataaggaga gagagaaaag cctaaccagt                                30

<210> SEQ ID NO 10
<211> LENGTH: 19
<212> TYPE: DNA
<213> ORGANISM: Artificial
<220> FEATURE:
<223> OTHER INFORMATION: Primer

<400> SEQUENCE: 10
accaagaact cgttagatc                                            19

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11

-continued

```
aacgcatata actaaagatc                                                 20

<210> SEQ ID NO 12
<211> LENGTH: 26
<212> TYPE: DNA
<213> ORGANISM: Artificial
<220> FEATURE:
<223> OTHER INFORMATION: Primer

<400> SEQUENCE: 12
ccatggatcc agagacgaag cgaaac                                          26

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
actccatgga taataactgg ttaggc                                          26

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
aaattctcaa gctttggtcc atcttg                                          26

<210> SEQ ID NO 15
<211> LENGTH: 555
<212> TYPE: PRT
<213> ORGANISM: Arabidopsis thaliana

<400> SEQUENCE: 15

Met Lys Ser Phe Cys Asp Asn Asp Asp Asn Asn His Ser Asn Thr Thr
1               5                   10                  15

Asn Leu Leu Gly Phe Ser Leu Ser Ser Asn Met Met Lys Met Gly Gly
                20                  25                  30

Arg Gly Gly Arg Glu Ala Ile Tyr Ser Ser Ser Thr Ser Ser Ala Ala
            35                  40                  45

Thr Ser Ser Ser Ser Val Pro Pro Gln Leu Val Val Gly Asp Asn Thr
        50                  55                  60

Ser Asn Phe Gly Val Cys Tyr Gly Ser Asn Pro Asn Gly Gly Ile Tyr
65                  70                  75                  80

Ser His Met Ser Val Met Pro Leu Arg Ser Asp Gly Ser Leu Cys Leu
                85                  90                  95

Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
        115                 120                 125

His Lys Glu Ala Met Asp Leu Ser Leu Asp Ser Leu Phe Tyr Asn Thr
    130                 135                 140

Thr His Glu Pro Asn Thr Thr Thr Asn Phe Gln Glu Phe Phe Ser Phe
145                 150                 155                 160

Pro Gln Thr Arg Asn His Glu Glu Glu Thr Arg Asn Tyr Gly Asn Asp
                165                 170                 175
```

```
Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
            195                 200                 205

Cys Ile Thr Gly Ser His His His Gln Gln Asn Gln Asn Gln Asn His
            210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Lys Lys Lys Arg Gly
                245                 250                 255

Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
            275                 280                 285

Arg His Arg Trp Thr Gly Arg Tyr Glu Ala His Leu Trp Asp Asn Ser
            290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
            355                 360                 365

Val Ala His Leu Arg Arg Lys Ser Ser Gly Phe Ser Arg Gly Ala Ser
            370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
            435                 440                 445

Val Asp Arg Ile Met Ser Ser Asn Thr Leu Leu Ser Gly Glu Leu Ala
450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
            500                 505                 510

Asn Gln Lys Met Phe Gly Ser Asn Met Gly Gly Asn Met Ser Pro Trp
            515                 520                 525

Thr Ser Asn Pro Asn Ala Glu Leu Lys Thr Val Ala Leu Thr Leu Pro
            530                 535                 540

Gln Met Pro Val Phe Ala Ala Trp Ala Asp Ser
545                 550                 555

<210> SEQ ID NO 16
<211> LENGTH: 485
<212> TYPE: PRT
<213> ORGANISM: Sea mays
```

-continued

<400> SEQUENCE: 16

```
Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Gln Gly Ala Val Glu Glu Ser
        35                  40                  45

Pro Arg Thr Val Glu Asp Phe Leu Gly Gly Val Gly Cys Val Gly Ala
    50                  55                  60

Pro Arg Ser Arg Arg Leu Gln Ile Arg Ile Thr Ser Leu Cys Ala Ala
65                  70                  75                  80

Ser Cys Gly Ser Ile Thr Ala Arg Phe Leu Arg His Tyr Pro Ala Ala
                85                  90                  95

Gln Ser Gly Thr Thr Val Gly Glu Pro Leu Ser Arg Phe Thr Leu Ala
                100                 105                 110

Ala Met Ser Ser Thr Asp Val Ala Trp Ala Glu Ser Asp Gln Ala Ser
            115                 120                 125

Arg Ser Ala Glu Thr Phe Gly Gln Arg Thr Ser Ile Tyr Arg Gly Val
130                 135                 140

Thr Arg His Arg Trp Thr Gly Arg Tyr Glu Ala His Leu Trp Glu Asn
145                 150                 155                 160

Ser Cys Arg Arg Glu Gly Gln Ser Arg Lys Gly Arg Gln Val Tyr Leu
                165                 170                 175

Gly Gly Tyr Asp Lys Glu Glu Lys Ala Ala Arg Ala Tyr Asp Leu Ala
            180                 185                 190

Ala Leu Lys Phe Trp Gly Pro Thr Thr Thr Thr Asn Phe Gln Val Ser
            195                 200                 205

Asn Tyr Glu Lys Glu Leu Glu Glu Met Lys Ser Met Thr Arg Gln Glu
210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
                245                 250                 255

Ala Arg Ile Gly Ser Val Ala Gly Asn Lys Asp Leu Tyr Leu Gly Thr
            260                 265                 270

Phe Ser Thr Gln Glu Glu Ala Ala Glu Ala Tyr Asp Ile Ala Ala Ile
        275                 280                 285

Lys Phe Arg Gly Leu Asn Ala Val Thr Asn Leu Asp Met Ser Arg Tyr
290                 295                 300

Asp Val Glu Ser Ile Leu Ser Ser Asp Leu Pro Val Gly Gly Gly Ala
305                 310                 315                 320

Ser Gly Arg Ala Ala Ala Lys Phe Pro Leu Asp Ser Leu Gln Pro Gly
                325                 330                 335

Ser Ala Ala Ala Met Met Leu Ala Gly Ala Ala Ala Ser Gln Ala
            340                 345                 350

Thr Met Pro Pro Ser Glu Lys Asp Tyr Trp Ser Leu Leu Ala Leu His
            355                 360                 365

Tyr Gln Gln Gln Gln Glu Gln Glu Arg Gln Phe Pro Ala Ser Ala Tyr
    370                 375                 380

Glu Ala Tyr Gly Ser Gly Gly Val Asn Val Asp Phe Thr Met Gly Thr
385                 390                 395                 400

Ser Ser Gly Ser Asn Asn Asn Thr Gly Ser Gly Val Met Trp Gly Ala
                405                 410                 415
```

```
Thr Ser Gly Ala Val Val Gly Gln Gln Asp Ser Ser Lys Gln Gly
            420                 425                 430

Asn Gly Tyr Ala Ser Asn Ile Pro Tyr Ala Ala Met Val Ser Gly
            435                 440                 445

Thr Ala Gly Tyr Glu Gly Ser Thr Gly Asp Asn Gly Thr Trp Val Thr
450                 455                 460

Thr Thr Thr Ser Ser Asn Thr Gly Thr Ala Pro His Tyr Tyr Asn Tyr
465                 470                 475                 480

Leu Phe Gly Met Glu
                485

<210> SEQ ID NO 17
<211> LENGTH: 446
<212> TYPE: PRT
<213> ORGANISM: Sea mays

<400> SEQUENCE: 17

Met Ala Ala Thr Arg Arg Ala Phe Phe His Ser Ala Val Asp Gly Ile
1               5                   10                  15

Ala Arg Ala Gly Pro Gly Glu Ala Glu Arg Leu Pro Ala Pro Pro Gln
                20                  25                  30

Val Gly Arg Pro Val Glu Gly Ala Ser Ser Met Val Leu Gly Phe Pro
            35                  40                  45

Val Pro Arg Pro Thr Met Pro Asp Arg Arg Pro Ala Ala Val Thr Gln
50                  55                  60

Gln Phe Phe Pro Pro Thr Thr Thr Ala Ala Gln Gln Ala Thr Met Glu
65                  70                  75                  80

Glu Gln Cys His Val Pro Ala Gly Ser Ala Ala Glu Gln Trp Val Arg
                85                  90                  95

Ser Ser Ala Ser Arg Lys Ser Arg Arg Gly Pro Arg Ser Arg Ser Ser
            100                 105                 110

Gln Tyr Arg Gly Val Thr Phe Tyr Arg Arg Thr Gly Arg Trp Glu Ser
        115                 120                 125

His Ile Trp Asp Cys Gly Lys Gln Val Tyr Leu Gly Gly Phe Asp Thr
130                 135                 140

Ala Gln Ala Ala Ala Arg Ala Tyr Asp Gln Ala Ala Ile Lys Phe Arg
145                 150                 155                 160

Gly Leu Asn Ala Asp Ile Asn Phe Thr Leu Asp Asp Tyr Lys Asp Glu
                165                 170                 175

Met Lys Lys Met Lys Asp Leu Ser Lys Glu Glu Phe Val Leu Val Leu
            180                 185                 190

Arg Arg Gln Gly Ala Gly Phe Val Arg Gly Ser Ser Arg Phe Arg Gly
        195                 200                 205

Val Thr Gln His Lys Cys Gly Lys Trp Glu Ala Arg Ile Gly Gln Leu
210                 215                 220

Met Gly Lys Lys Tyr Val Tyr Leu Gly Leu Tyr Asp Thr Glu Thr Glu
225                 230                 235                 240

Ala Ala Gln Ala Tyr Asp Lys Ala Ala Ile Lys Cys Tyr Gly Lys Glu
                245                 250                 255

Ala Val Thr Asn Phe Asp Ala Gln Ser Tyr Asp Lys Glu Leu Gln Ser
            260                 265                 270

Gln Pro Trp Asp Gly Glu Leu Asp Leu Glu Leu Ser Leu Gly Cys Ala
        275                 280                 285

Ser Ser Asp Pro Ser Thr Val Ala Val Glu Ala Phe Ser Pro Ala Thr
```

-continued

```
              290                 295                 300
Ser Ser Ser Ser Arg Lys Gln Arg Thr Met Thr Leu Thr Leu Gly Leu
305                 310                 315                 320

Pro Glu Glu Glu Thr Gly Ala Gly Tyr Pro His Pro Ala Ala Gly
                325                 330                 335

Met Phe Gly Arg Pro Ala Asp Gly His Val His Val Ala Pro Pro Pro
                340                 345                 350

His Arg Gln Trp Gln Gln Gln Gln Gly Gln His Ala Ala Pro Asp
                355                 360                 365

Ala Ala Pro Glu Arg Arg Ala Glu Pro Ala Asp Arg Gln Arg Trp
370                 375                 380

Gly Arg Gly Ala Arg Trp Pro Ile Ala Ser Ala Ser Gly Ile Asn Trp
385                 390                 395                 400

Ala Trp Ala Pro Pro Tyr Ala Thr Ala Arg Ala Gly Thr Asp Asp Asp
                405                 410                 415

Asp Ala Ser Ala Ala Ala Ala Ser Ser Gly Phe Pro Leu Trp
                420                 425                 430

Gln Leu Gly Ala Ala Ser Ser Arg Ser Ser Trp Pro Ser Cys
                435                 440                 445
```